United States Patent
Bolzoni

(10) Patent No.: US 12,412,573 B2
(45) Date of Patent: Sep. 9, 2025

(54) MACHINE LEARNING-BASED INTERACTIVE CONVERSATION SYSTEM

(71) Applicant: ItsAllAbout, Inc., Los Angeles, CA (US)

(72) Inventor: Damiano Bolzoni, Los Angeles, CA (US)

(73) Assignee: ItsAllAbout, Inc., Los Angeles, CA (US)

( * ) Notice: Subject to any disclaimer, the term of this patent is extended or adjusted under 35 U.S.C. 154(b) by 320 days.

(21) Appl. No.: 17/865,833

(22) Filed: Jul. 15, 2022

(65) Prior Publication Data

US 2024/0021196 A1  Jan. 18, 2024

(51) Int. Cl.
| | |
|---|---|
| *G10L 15/22* | (2006.01) |
| *G06F 16/21* | (2019.01) |
| *G06F 16/28* | (2019.01) |
| *G06V 20/40* | (2022.01) |
| *G06V 40/20* | (2022.01) |
| *G10L 15/30* | (2013.01) |
| *G10L 25/57* | (2013.01) |

(Continued)

(52) U.S. Cl.
CPC ............ *G10L 15/22* (2013.01); *G06F 16/219* (2019.01); *G06F 16/285* (2019.01); *G06V 20/40* (2022.01); *G06V 40/20* (2022.01); *G10L 15/30* (2013.01); *G10L 25/57* (2013.01); *G10L 25/63* (2013.01); *G16H 20/70* (2018.01)

(58) Field of Classification Search
CPC ......... G10L 15/22; G10L 15/30; G10L 25/57; G10L 25/63; G06F 16/219; G06F 16/285; G06V 20/40; G06V 40/20; G16H 20/70

USPC ........................................................ 704/251
See application file for complete search history.

(56) References Cited

U.S. PATENT DOCUMENTS

| 11,295,731 B1 * | 4/2022 | Wong ...................... H04L 51/02 |
| 2021/0110894 A1 * | 4/2021 | Shriberg ................ G16H 50/50 |

(Continued)

FOREIGN PATENT DOCUMENTS

| CN | 113728341 A | * 11/2021 | ........... G10L 15/063 |
| KR | 20210015010 A | * 2/2021 | ............. G16H 10/20 |

OTHER PUBLICATIONS

Robinson, Ann. "Meet Ellie, the machine that can detect depression", The Guardian, Sep. 17, 2015 (3 pages).

(Continued)

*Primary Examiner* — Edwin S Leland, III
(74) *Attorney, Agent, or Firm* — WOMBLE BOND DICKINSON (US) LLP

(57) ABSTRACT

Systems and methods for implementing an interactive conversation platform that can engage in conversation with a user in a manner that simulates humanistic interaction. A response to a prompt issued by a state machine that facilitates interaction by the user with an interactive conversation application may be received from the user. The prompt corresponds to a current state that is one of a plurality of states that the state machine may operate in, and each of the plurality of states has a corresponding prompt. Metadata comprising information about the user may be extracted from the response and used to enrich the response. A subsequent state of the plurality of states that the state machine is to transition to from the current state may be determined based at least in part on the enriched response and the state machine may transition to the subsequent state.

30 Claims, 13 Drawing Sheets

(51) Int. Cl.
  *G10L 25/63*   (2013.01)
  *G16H 20/70*   (2018.01)

(56) References Cited

U.S. PATENT DOCUMENTS

| | | | | |
|---|---|---|---|---|
| 2021/0369042 A1* | 12/2021 | Gustman | ............ | B65D 85/8046 |
| 2023/0102807 A1* | 3/2023 | Rudi | ................. | H04N 21/4394 |
| | | | | 725/32 |
| 2024/0021196 A1* | 1/2024 | Bolzoni | ................ | G06F 16/285 |
| 2024/0069858 A1* | 2/2024 | Bolzoni | ................ | G06F 3/167 |

OTHER PUBLICATIONS

PCT Search Report and Written Opinion from related PCT Application No. PCT/US2023/070153, mailed on Nov. 9, 2023, 12 pages.

* cited by examiner

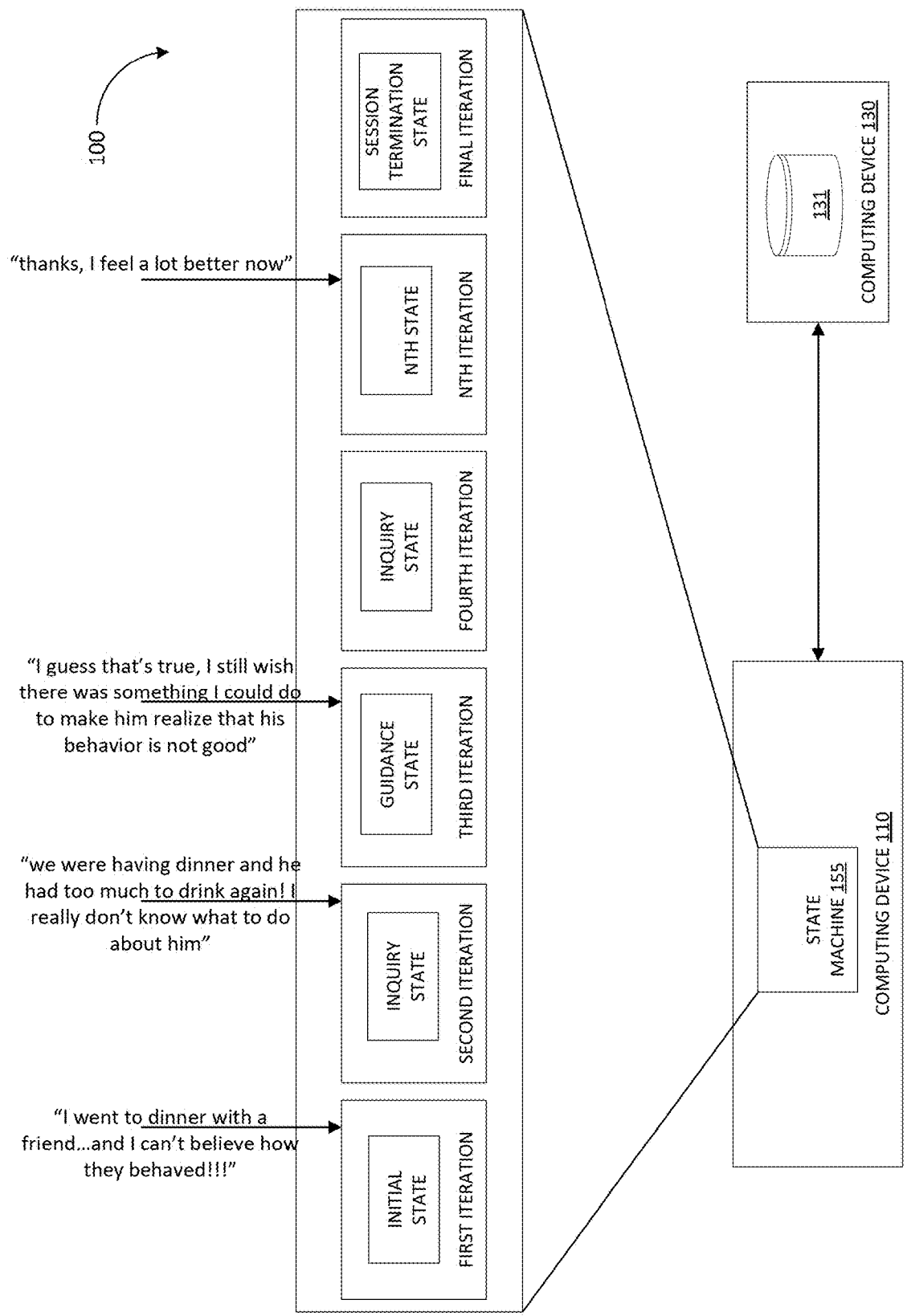

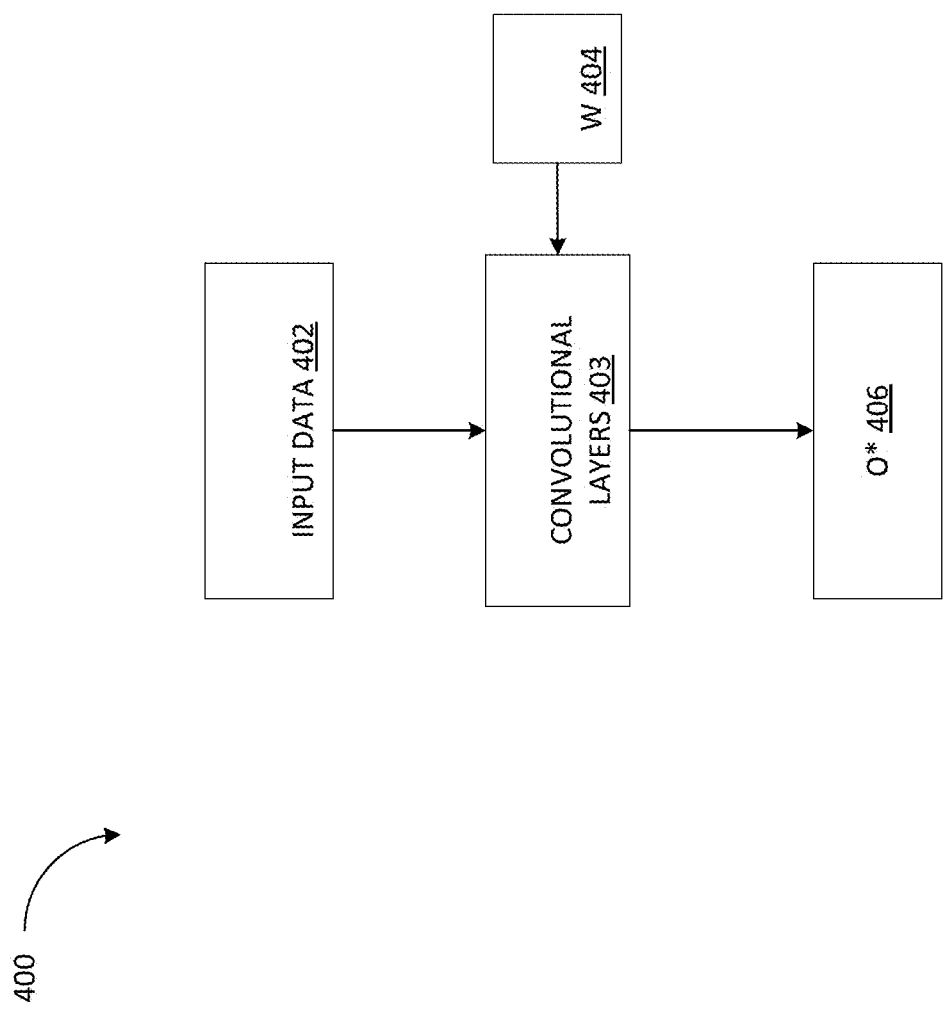

MACHINE LEARNING-BASED INTERACTIVE CONVERSATION SYSTEM

TECHNICAL FIELD

Aspects of the present disclosure relate to interactive wellness systems, and more particularly, to machine learning-based interactive wellness systems.

BACKGROUND

Seeing a therapist enables many people to discuss and address issues they are dealing with in their lives. As a person trained to listen and analyze, a therapist can comfort a person by showing emotion (e.g., empathy), sharing emotion with a person (e.g., smiling if a person smiles), analyzing current and past behaviors to identify root causes of a persons issues, and performing other actions that are traditionally associated with human interaction. However, therapy with a professional therapist can be expensive (thus limiting the number of people who can utilize it) and is not usually offered on an on-demand basis.

A chat program (also referred to as a "chatbot") is a software application used to conduct a chat conversation (either on-line or off-line) via text or text-to-speech, in lieu of providing direct contact with a live human agent. Chat programs are used in dialog systems for various purposes including customer service, request routing, or information gathering. While some chat programs use extensive word-classification processes, natural language processors, and sophisticated AI, others simply scan for general keywords and generate responses using common phrases obtained from an associated library or database.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

FIG. 2C is a block diagram illustrating state transitions as an interactive conversation application progresses through a user session, in accordance with some embodiments of the present disclosure.

FIG. 4A is a diagram illustrating the structure of a machine learning model.

DETAILED DESCRIPTION

Many chat programs are not interactive, and are limited in the way they can provide information/content (e.g., a user can only choose a topic and then listen to a predefined recording). Other chat programs are limited in the way a user can interact with the program (e.g., can only type messages via a keyboard and receive messages in text format via a traditional chat GUI on a display), and are thus unable to adequately convey and share emotions (e.g., the chat program cannot smile in response to a user smiling, and cannot cry along with a user in response to the user crying).

Many chat programs are designed to convincingly simulate the way a human would behave as a conversational partner, but typically require continuous tuning and testing. Despite these efforts, they are often unable to adequately converse with a user and have other limitations that hinder a truly humanistic experience. For example, chat programs cannot recall previous events/information and identify patterns and root causes associated with issues a user is experiencing.

The present disclosure addresses the above-noted and other deficiencies by providing an interactive conversation platform that can engage in conversation with a user in a manner that simulates humanistic interaction including emotion recognition and learned understanding of users. More specifically, the present disclosure addresses the above-noted and other deficiencies by using a processing device to receive from a user, a response to a prompt issued by a state machine that facilitates interaction by the user with an interactive conversation application, wherein the prompt corresponds to a current state that is one of a plurality of states that the state machine may operate in, and each of the plurality of states has a corresponding prompt comprising a set of statements and/or questions that are designed to achieve the particular objective of that state (e.g., find out more about an event that is troubling the user). The processing device may extract from the response, metadata comprising information indicating an emotional state of the user and enrich the response with the metadata. The processing device may determine, using a machine learning (ML) algorithm and a rule-based approach, a subsequent state from the plurality of states that the state machine is to transition to from the current state based at least in part on the enriched response and transition the state machine to the subsequent state. This process is performed iteratively, with each iteration being defined by a prompt issued by the state machine and the user's response thereto. The state machine may transition to various states throughout the course of a conversation. At the end of each iteration, the user's responses may be saved in a user profile, which the state machine may utilize to learn about the user over time, and which may help inform state transition decisions.

Figure 1A:
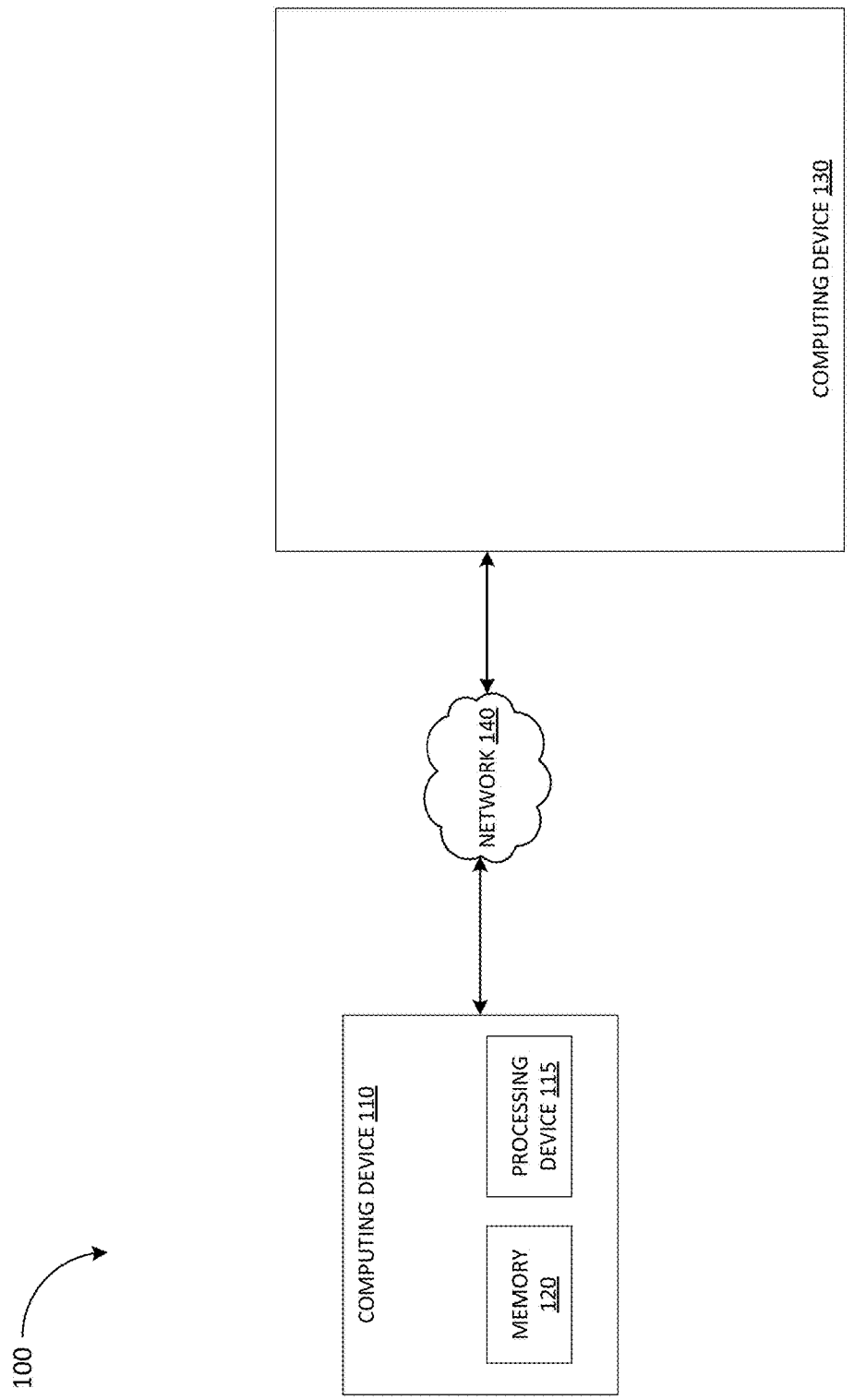
FIG. 1A is a block diagram that illustrates an example system for implementing an interactive conversation application, in accordance with some embodiments of the present disclosure.

FIG. 1A is a block diagram that illustrates an example system 100 in which embodiments of the present disclosure may be realized. As illustrated in FIG. 1, the system 100 includes a computing device 110 and a computing device 130. The computing devices 110 and 130 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a WiFi™ hotspot connected with the network 140 and/or a wireless carrier system that can be implemented using various data processing equipment, communication towers (e.g. cell towers), etc. In some embodiments, the network 140 may be an L3 network. The network 140 may carry communications (e.g., data, message, packets, frames, etc.) between computing device 110 and computing device 130. Each computing device 110 and 130 may include hardware such as processing device 115 (e.g., processors, central processing units (CPUs), memory 120 (e.g., random access memory 120 (e.g., RAM), storage devices (e.g., hard-disk drive (HDD), solid-state drive (SSD), etc.), and other hardware devices (e.g., one or more cameras, a microphone, a display, a keyboard, a sound card, a video card, etc.). In some embodiments, memory 120 may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a monolithic/single device or a distributed set of devices. Memory 120 may be configured for long-term storage of data and may retain data between power on/off cycles of the computing device 110.

Each of the computing devices 110 and 130 may comprise any suitable type of computing device or machine that has a programmable processor including, for example, server computers, desktop computers, laptop computers, tablet computers, smartphones, set-top boxes, etc. In some embodiments, one or more of the computing devices 110 and 130 may comprise any appropriate smart device or home automation controller such as e.g., Amazon's Alexa™ platform. In addition, one or more of the computing devices 110 and 130 may comprise a computing device that provides virtual and/or augmented reality functionality. In some examples, each of the computing devices 110 and 130 may comprise a single machine or may include multiple interconnected machines (e.g., multiple servers configured in a cluster). The computing devices 110 and 130 may be implemented by a common entity/organization or may be implemented by different entities/organizations. For example, computing device 110 may be operated by a first company/corporation and one or more computing devices 130 may be operated by a second company/corporation. Each of computing device 110 and computing devices 130 may execute or include an operating system (OS) (not shown) which may manage the execution of other components (e.g., software, applications, etc.) and/or may manage access to the hardware (e.g., processors, memory, storage devices etc.) of the computing device.

Figure 1B:
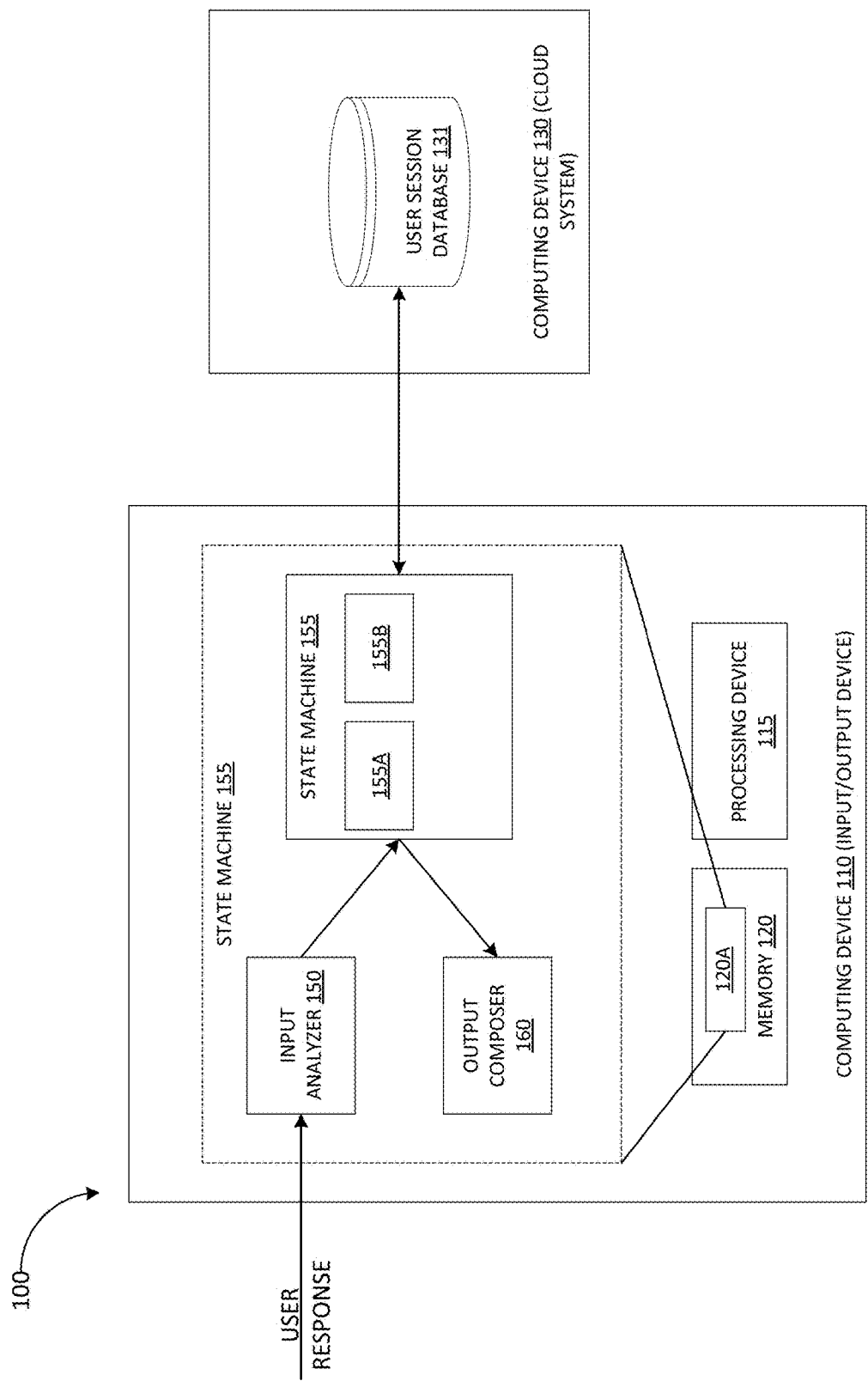
FIG. 1B is a block diagram that illustrates a detailed view of an example system for implementing an interactive conversation application, in accordance with some embodiments of the present disclosure.

FIG. 1B illustrates a detailed view of the system 100. The memory 120 may include an interactive wellness application 120A which may be a software module executed by the processing device 115 to perform one or more of the functions associated with providing an interactive conversation platform that can engage in conversation with a user in a manner that simulates humanistic interaction, in accordance with embodiments of the present disclosure as described herein. The interactive wellness application 120A may comprise three individual components including an input analyzer 150, a state machine 155, and an output composer 160. Upon execution of the interactive wellness application 120A, a user interface comprising an avatar (such as avatar 350 shown in FIG. 3B) may be provided (e.g., on a display of the computing device 110). The user may interact with the interactive wellness application 120A via the avatar 350 as discussed in further detail herein. Embodiments of the present disclosure may refer to the user's interaction with the avatar 350 and the interactive wellness application 120A, and it should be noted that the user's interaction with the avatar 350 and the interactive wellness application 120A are used interchangeably herein. The user may utilize various components of computing device 110 including the cameras, the microphone, and the keyboard to interact with the interactive wellness application 120A.

The input analyzer 150 may function to receive and process user interactions with the interactive wellness application 120A. More specifically, the input analyzer 150 may communicate with the cameras, the microphone, and the keyboard of the computing device 110 to facilitate video, voice (e.g. spoken) and text (e.g., typed) user interactions with the interactive wellness application 120A. For example, in response to prompts by the wellness application 120A (delivered via the avatar 350), the user may vocalize their response to the prompts by speaking into the microphone or typing their response on the keyboard. A prompt as used herein may comprise one or more statements and/or questions designed to engage the user in discussion about a topic(s) of relevance. When analyzing an audio/spoken input from the user, the input analyzer 150 may convert the audio input into text for further processing using any appropriate "speech-to-text" techniques. In some embodiments, the input analyzer 150 may utilize on-board speech-to-text capabilities of the computing device 110, while in other embodiments the input analyzer 150 may utilize a remote service such as the AWS' speech-to-text service (which may be running e.g., on the computing device 130).

The input analyzer 150 may analyze the text of user responses (whether typed by the user or generated as a result of speech-to-text processing) to extract response metadata comprising information relevant to the user from the text. The input analyzer 150 may extract response metadata including e.g., people, dates, events, and issues that are the subject of the user's response as well as an emotional state of the user, and may enrich the text of their response with the response metadata. More specifically, the input analyzer 150 may add the response metadata to the text of the user's response so that the state machine 155 may utilize such metadata when determining a next state for the user session (as discussed in further detail herein). This enables the interactive wellness application 120A to "humanize" its interaction with the user by allowing it to account for factors such as the current emotional state of the user, previous interactions with the user, and other information when determining a next prompt to output to the user (as discussed in further detail herein). The input analyzer 150 may comprise any appropriate machine learning (ML) algorithm(s) such as natural language processing algorithms and/or neural networks to extract the response metadata (relevant information) from the text of the user's response. For instance, the input analyzer 150 may utilize the named entity recognition class of algorithms to extract relevant entities (e.g., people, places, events, issues) from the text of the user's response. In another example, the input analyzer 150 may additionally or alternatively leverage any suitable pattern matching algorithms (that match sentences and words to recognize constituent patterns) to look for specific key words/phrases or a specific set of key words/phrases from the text of the user's response that indicate e.g., relevant entities, an emotional state of the user, and other response metadata. In a further example, the input analyzer 150 may additionally or alternatively utilize text categorization algorithms to analyze sentences with the aim of assigning predefined categories to them. In some embodiments, the input analyzer 150 may additionally or alternatively leverage any appropriate neural network model to predict emotion from user responses. In some embodiments, the input analyzer 150 may deploy ML model(s) utilizing a framework for creating, importing, testing, and improving ML models such as a Hugging Face transformers framework. For example, an ML model such as e.g., PyTorch could be loaded into the hugging face transformers framework and be executed to predict emotions/feelings (i.e., the emotional state of the user) from user responses.

It should be noted that the emotional state of the user may correspond to feelings (e.g., anger, sadness, joy etc.) that the user is currently experiencing as a result of one or more issues that are affecting their life (and that they are seeking to discuss with the interactive wellness application 120A) and may be indicated by the words/language of their responses as well as physical indicators that accompany their responses when their responses are provided via voice and/or video as discussed in further detail herein. Thus, the emotional state of the user may change from iteration to iteration of the user session, as the user engages with the interactive wellness application 120A to begins to resolve their issue(s).

In some embodiments, when the user has provided their responses to prompts from the application 120A by speaking into the microphone, the input analyzer 150 may also analyze the captured audio signals corresponding to the user's response to extract metadata indicating the emotional state of the user. The processing device 115 (via the input analyzer 150) may perform this analysis using any (or a combination) of several audio analysis techniques. For example, the input analyzer 150 may perform a static analysis of audio frequencies of the user's response, e.g., to determine whether the user is crying or upset. In another example, the input analyzer 150 may also utilize one or more neural networks that are trained to detect emotions from audio signals by analyzing physical indicators of the user's emotional state such as the pitch, tone, and words per minute of the user's response, in addition to other features such as tendency to stop talking/pauses in speech, and a decrease or increase in volume as the user provides their response. The input analyzer 150 may generate one or more emotional indicators (e.g., happy, sad, angry, crying etc.) of the user's emotional state based on the physical indicators of the user's emotional state and add these emotional indicators along with the physical indicators of the user's emotional state to the response metadata that is extracted from the text of the user's response In addition, if the user has provided his input via camera (as well as via microphone and/or keyboard), the input analyzer 150 may analyze video frames of the user's face/body captured by the camera during their response to extract additional metadata indicating the user's emotional state. For example, the input analyzer 150 may utilize one or more neural networks to analyze muscle movements, facial expressions, so-called facial landmarks, whether the user is facing the camera or looking away, and the user's posture (sitting/standing, shoulders hunched etc.), among other physical indicators indicating the user's emotional state. Such physical indicators may also be used to determine other characteristics of a person (i.e., gender, age, etc.). The input analyzer 150 may generate (accounting for physical indicators extracted from the captured audio signals as well) one or more emotional indicators (e.g., happy, sad, angry, crying etc.) of the user's emotional state and add these emotional indicators along with the physical indicators of the user's emotional state to the response metadata that is extracted from the text of the user's response. As discussed in further detail herein, the response metadata may enable the interactive wellness application 120A to "humanize" its interaction with the user by allowing it to account for factors such as the current emotional state of the user, previous interactions with the user, and other information when determining a next prompt to output to the user (as discussed in further detail herein). The input analyzer 150 may utilize a separate neural network (from the one used to extract response metadata from the text of the user's response) for analysis of the physical indicators, and in some embodiments, may utilize a separate neural network for analyzing each of the physical indicators. For example, the input analyzer 150 may utilize PyTorch, which is an open source machine learning library used for computer vision and natural language processing. In some embodiments, the input analyzer 150 may utilize any appropriate third party service that offers pre-trained and customizable computer vision capabilities to extract information about facial expressions and emotions from images and videos.

It should be noted that in some embodiments when the user's response is provided only via audio and/or video, the input analyzer may refrain from converting the user's response to text, and may directly analyze the audio and video data of the user's response as discussed hereinabove to extract response metadata indicating (among other information) the emotional state of the user.

Upon extracting the response metadata from the text of the user's response and enriching the text of the user's response with the response metadata, the input analyzer 150 may transmit the enriched text to the state machine 155. It should be noted that although illustrated as implemented within the computing device 110, the input analyzer 150 could be executed remotely (e.g., on computing device 130 as a cloud service that the interactive wellness application 120A communicates with). In some embodiments, the functions of the input analyzer 150 may be implemented by both the computing device 110 and computing device 130 (a remote/cloud service) with each device implementing certain functions of the input analyzer 150.

The user's interaction with the interactive wellness application 120A (hereinafter referred to as the user session) may be an iterative process, where each iteration is defined by a prompt provided to the user by the interactive wellness application 120A and a user's response thereto. More specifically, the prompt provided to the user by the interactive wellness application 120A at each iteration may be based on a state (from among a plurality of states) that the state machine 155 is in during that iteration. Each of the plurality of states may be associated with a particular predefined prompt (e.g., sentence(s)/statement(s), question(s)) that can be output by the state machine 155 upon the state machine 155 transitioning to that state. The state machine 155 may transition through a number of different states over the course of a user session, where each different state represents a particular objective that the interactive wellness application 120A is to accomplish during an iteration (e.g., reducing the user's anxiety, or obtaining more information about an issue that is causing the user anxiety).

The predefined prompt associated with a state may be a base prompt geared towards accomplishing the state's objective and can be modified by the output composer 160 (i.e., further tailored to the user by the output composer 160 as discussed in further detail herein) based on a number of factors before being output to the user, as discussed in further detail herein. For example, the plurality of states of the state machine 155 may include an initial state where the interactive wellness application 120A may ask an introductory question and/or make an introductory statement meant to elicit a response from the user regarding a topic they would like to discuss/that is causing the user anxiety (the predefined prompt of the initial state). For example, the predefined prompt of the initial state may comprise a phrase such as "what is bothering you today?," "how are you feeling?," or "what issues would you like to discuss today?" The initial state may serve as a starting point of the user session. The state machine 155 may be responsible for determining whether or not it should transition to a new state at the next iteration of the user session, and if so, which state it should transition to based on the enriched text of the user's response (to the prompt of the current state of the user session) as well as a number of other variables, as discussed in further detail herein.

Based on the user's response (processed and enriched by the input analyzer 150) to the prompt of the initial state and other factors (as described in further detail herein), the state machine 155 may determine a state it should transition to during the next iteration of the user session (or determine that it should remain in the current state during the next iteration of the user session). Another example state may be an inquiry state where the state machine 155's objective may be to attempt to elicit further details about an event or issue of relevance using a predefined prompt such as "tell me more about what happened during the event" or "how did that make you feel?" Yet another example state may be a guidance state, where the state machine 155's objective is to provide the user guidance on how to deal with the issues of relevance, and thus the interactive wellness application 120A may provide the user with a predefined prompt such as "try to understand where this person is coming from" or "always take a deep breath when you feel yourself getting upset." During a user session, there may not be a linear transition through states, and the state machine 155 may transition back and forth between certain states before moving to other states based on the user's response (and other factors discussed in further detail herein) at each iteration during the user session. In addition, there may be multiple "versions" of a particular state for the state machine 155 to transition to. For example, a first version of an inquiry state may have a base prompt of "tell me more about this event," while a second version of the inquiry state may have a base prompt of "why do you think this person took that particular action?"

During each iteration of a user session (e.g., upon determining a next state to transition to), the state machine 155 (via the processing device 115) may store the user's responses (enriched to include response metadata extracted by the input analyzer 150) in a user session database 131 (hereinafter referred to as database 131) of computing device 130 as shown in FIG. 1B. The database 131 may also include the prompt issued by the interactive wellness application 120A during the current iteration and the prompts issued and (metadata enriched) user responses received during each previous iteration of a current user session as well as each iteration of previous user sessions (referred to herein as the "user profile"). In some embodiments, the state machine 155 may only store metadata that is extracted from user responses in the database 131 (user profile). In other embodiments, the state machine 155 may store the user responses themselves along with any metadata extracted therefrom in the database 131. In this way, as more and more iterations are processed, the interactive wellness application 120A may learn more and more about the user and may begin making inferences that can be saved as part of the user profile and factored in to the state machine 155's state transition decisions. When determining a state to transition to, the state machine 155 may fetch the user profile and consider it as one factor when making state transition decisions as discussed in further detail herein. Stated differently, the interactive wellness application 120A may use the database 131 to recognize patterns/identify elements that are common to a number of user responses in order to learn about the user and enrich the conversation that the user can have with it based on its knowledge of the user. For example, the interactive wellness application 120A may be able to more accurately identify events, situations, actions, and/or people that are the root cause of a user's issues based on repeated mention (e.g., in an angry tone of voice) of particular situations and/or particular people over time and an emotional state of the user associated with discussion of those particular situations and/or particular people. The interactive wellness application 120A may also infer, based on the user profile, a personality type and other information about the user which may aid in providing effective conversation.

To determine the next state to transition to during a current iteration of the user session, the state machine 155 may consider several variables, including but not limited to the previous state of the user session (if any), the user's response during the current state including response metadata extracted therefrom by the input analyzer 150, a classification of the user's response during the current state into a particular category among a set of predefined categories (e.g., defense, neutral, feeling, anxiety, as discussed in further detail herein), and data from the user profile including the user's responses from previous iterations/states of the user session as well as previous user sessions including metadata (i.e., response metadata) extracted therefrom (e.g., any party the user is/was having issues with, identification of the issues that were/are relevant, how the user is/was feeling).

With respect to the classification of the user response during the current state, the state machine 155 may include a classification ML model 155A that has been trained to categorize/classify user responses into one of a set of predefined categories using training data comprising well-known user responses/sentences that have each been labeled with a corresponding category. The classification ML model 155 may comprise any appropriate ML model such as (by way of example and not limitation) a Transformers neural network (NN) that may then adopt the mechanism of self-attention and differentially weigh the significance of each part of the input data. Each of the categories in the set of predefined categories may correspond to a classification of a user response. Examples of categories in the set of predefined categories may include e.g., defensive, neutral, feeling, and anxiety. Thus, when the state machine 155 receives a user response, it may utilize the classification ML model 155A to identify similarities/determine a similarity measure between the received user response and the well-known user responses/sentences it has been trained on. The classification ML model 155A may put the received user response into a "bin" corresponding to the category associated with the well-known user response/sentence (from the training data) that the received user response matches (or most closely matches). This categorization may be one factor that the state machine 155 considers when determining a next state to transition to (and whether transitioning to a new state is necessary at all). In addition, or alternatively to the use of ML algorithms, the state machine 155 may leverage static rules based on pattern matching algorithms, a set of keywords, or any combination of these techniques.

A classification of defensive may indicate that the user is blaming someone else, and not themselves for any issues they are experiencing. A neutral classification may indicate that no element in the user's response would indicate anything about the emotional content of the user's response. A classification of feeling may indicate that the user is feeling a particular emotion and an indication of that emotion, such as sadness, anger, or fear. A classification of anxiety may indicate that the user is anxious about something.

In some embodiments, the classification ML model 155A used by the state machine 155 to classify the user's response into one of the set of predefined categories may be trained based on training data comprising labeled well-known user responses themselves, as well as on the metadata extracted from those well-known user responses (i.e., the classification ML model 155A may be trained to categorize user responses based on well-known user responses and metadata extracted therefrom). As discussed hereinabove, the classification ML model 155A of the state machine 155 may comprise any appropriate ML model for classification of user responses such as e.g., the Transformers NN, or gpt2, which is an open source neural network pretrained model used for classifying user responses. For example, if the user's response states in part that e.g., "I was feeling sad because of a person's actions," or "I was feeling angry because of this event!," the state machine 155 may classify the user's response into the feeling category. Even if the user's response does not specifically mention an emotion, the classification ML model 155A may be trained to associate user responses that have metadata indicating an emotion (e.g., metadata indicating volume/tone of voice) with particular categories. For example, if the metadata of the user's response indicates that the user was feeling angry or sad (e.g., based on the volume of the user's voice or any other factors discussed herein), the state machine 155 may classify the user's response into the feeling category. If the user's response mentions physical symptoms, the state machine 155 may also use these to classify the response. For example, if the user's response merely discusses an event or person, the state machine 155 may classify this response as neutral, however if the user's response mentions chest pain or a headache in connection with discussing an event or person, the state machine 155 may classify the user's response as anxious. Similarly, if the user's response mentions that their heart was racing in connection with discussing an event, the state machine 155 may classify the user's response as anxious. In some embodiments, the state machine 155 may perform this classification using not only the classifier ML model 155A, but other ML algorithms, static rules based on pattern matching algorithms, a set of keywords, or any combination of these approaches.

As discussed herein, the state machine 155 may analyze/consider each of the variables mentioned above to determine a subsequent state to transition to. In some embodiments, while the classification ML model 155A performs the classification of the user's response, a state transition decision module 155B of the state machine 155 may govern how the classification of the user's response along with the additional variables listed above are used to determine a new state to transition to. In one example, an initial determination of the next state to transition to may be made based on the classification of the received user response by the classification ML model 155A, while the previous state of the user session (if any), the user's response including metadata extracted therefrom by the input analyzer 150 during the current state, and the user's responses from previous iterations/states of the user session as well as previous user sessions including metadata extracted therefrom (i.e., user profile) may be used by the state transition decision module 155B to fine-tune the initial determination of the next state to transition to and generate an ultimate determination of the next state to transition to. In some embodiments, the state machine 155 may assign each of the variables mentioned above a different weight, while in other embodiments each of the variables mentioned above may be averaged out in order to determine a next state to transition to. It should be noted that the state transition decision module 155B may utilize all of the variables mentioned above, or only a subset of them (e.g., 2 or 3 of them). The state transition decision module 155B may be implemented in any appropriate manner. For example, the state transition decision module 155B may utilize a separate ML model, a rule-based algorithm (e.g., that leverages static rules based on pattern matching algorithms), a set of keywords, or any combination of these techniques. In some embodiments, the state machine 155 may comprise an expert system that learns (using e.g., rule inference techniques) how a human operator would make state transition decisions and makes the ultimate determination of the next state to transition to. In still other embodiments, an expert system may replace the classifier ML model 155A and the state transition decision module 155B entirely.

In some embodiments, if the state machine 155 classifies a user's response during a current iteration as anxious, the state machine 155 may determine that the next state to transition to may be e.g., the anxiety relief state. In some embodiments, the state machine 155 may wait until the user's responses from e.g., a certain number of previous iterations/states of the user session indicate that the user has been feeling anxious (e.g., about a particular issue) before determining that it should transition to the anxiety relief state. The anxiety relief state may include predefined prompts geared towards alleviating stress and anxiety. The state machine 155 may continue in the anxiety relief state until it determines the user's anxiety has been lowered. For example, upon detecting that the user's responses for e.g., a consecutive number of iterations of the user session no longer indicate anxiety, the state machine 155 may determine that it should transition to the inquiry state to resume discussing the issue that initially caused the anxiety in the user to begin with.

Upon determining a new state to transition to, the state machine 155 may save the metadata extracted from the user's response and/or the user's response itself to the prompt of the current state in their user profile within database 131. The state machine 155 may pass the predefined prompt corresponding to the new state to the output composer 160, together with the user profile including user responses and metadata that were extracted from previous iterations of the user session and previous user sessions (thus, signaling the beginning of a new iteration of the user session). The prompt corresponding to the new state may comprise a base structure that can be modified with user specific words/phrases based on the aggregated information from the current iteration as well as information from the user profile. The output composer 160 may leverage all the information received from the state machine 155 to craft the appropriate response to return to the user (by modifying the base prompt of the selected state), and may output the response through the avatar 350 displayed on the display of computing device 110. The output composer 160 may be executed either within the computing device 110 as shown in FIG. 1B or remotely, for instance through a cloud-based infrastructure the computing device 110 communicates with (e.g., computing device 130), or as a mix of both. It should be noted that the output composer 160 may in some scenarios determine that no modification of the base structure of the predefined prompt for a new state is necessary, and output the unmodified predefined prompt.

In this way, the state machine 155 may engage in an iterative process where the user's responses to prompts (and metadata extracted therefrom) at each state are analyzed in the same way by the state machine 155 and the metadata is aggregated (in the database 131) throughout the iterations and is used continuously by the state machine 155 to inform state transition decisions (i.e., what kinds prompts to output) at future iterations of the user session. It should be noted that in some embodiments, the state machine 155 may aggregate both the user's responses to prompts and metadata extracted there from in the database 131 (as opposed to only the metadata extracted therefrom).

Figure 2A:
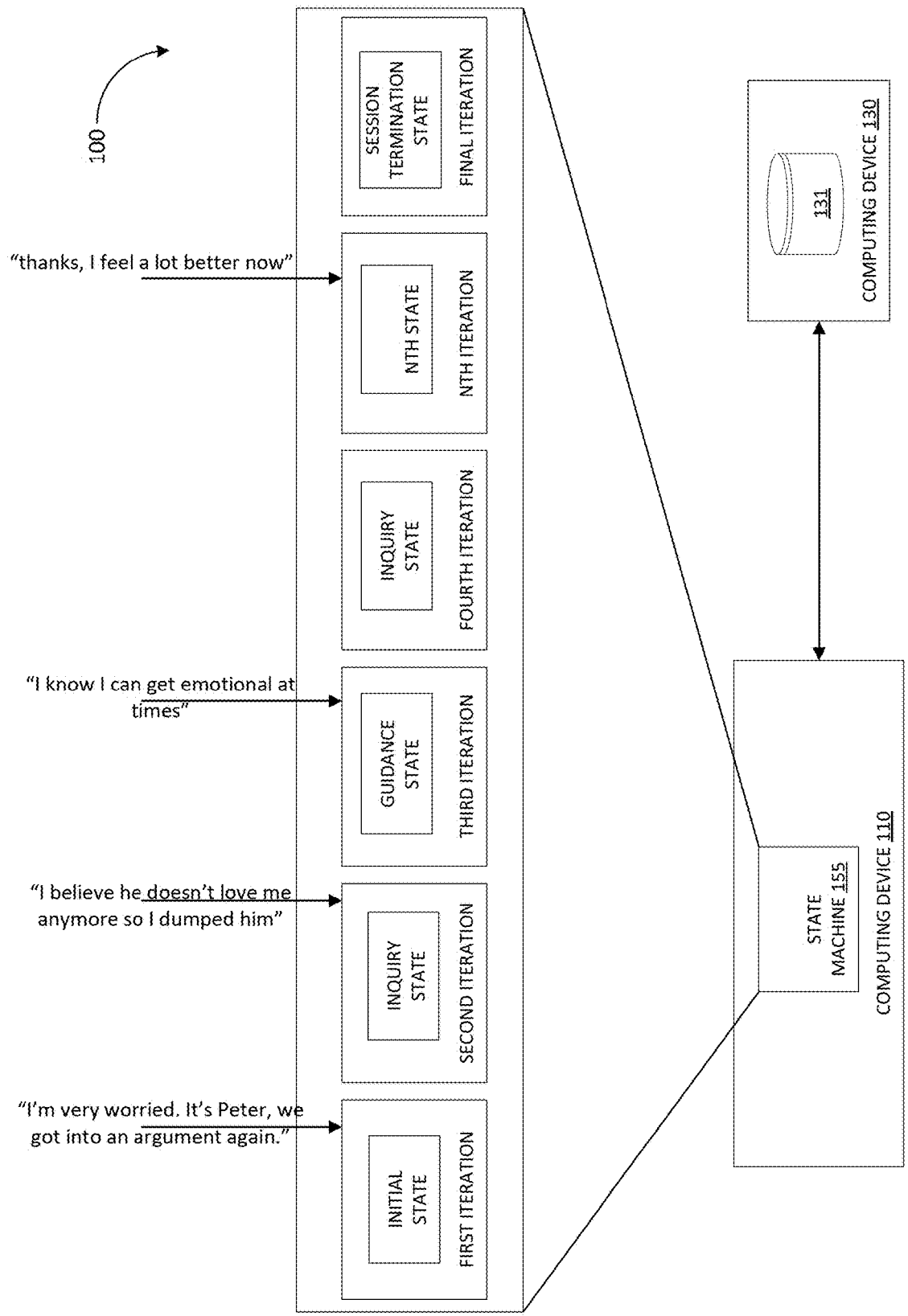
FIG. 2A is a block diagram illustrating state transitions as an interactive conversation application progresses through a user session, in accordance with some embodiments of the present disclosure.

FIG. 2A illustrates an example of a user session during which the user interacts with the application 120A. The user may execute the interactive wellness application 120A on computing device 110 in order to engage in a dialogue about an issue(s) (e.g., professional or personal issue) that they are experiencing in their life. The state machine 155 may begin the user session (i.e., the first iteration of the user session) at the initial state, which may be associated with a predefined prompt meant to elicit a response from the user regarding an issue(s) they would like to discuss. In the example of FIG. 2A, the predefined prompt may be "what issues would you like to discuss today?" The state machine 155 may output the predefined prompt of the initial state to the output composer 160.

In some embodiments, the state machine 155 may pass prompts associated with the initial state to the output composer 160 without any additional information (e.g., information from previous user sessions) and the output composer 160 may pass the prompt unmodified to the speakers and the display (utilizing the avatar 350) of the computing device 110. In other embodiments, the state machine 155 may pass prompts associated with the initial state to the output composer 160 with additional information from previous user sessions and the output composer 160 may modify the prompt before passing it to the speakers and the display of the computing device 110. For example, the state machine 155 may include metadata from one or more previous user sessions indicating that the user is having an argument with a particular person because of a particular issue. The output composer 160 may then modify the prompt to state e.g., "how are you doing? I remember you mentioned this particular issue, how are things going with that?" In the example of FIG. 2A, the state machine 155 passes the prompt of the initial state to the output composer 160 with no additional information so that it is provided to the user as is.

The user may reply (by speaking into the microphone in the example of FIG. 2A) that "I'm very worried. It's Peter, we got into an argument again." The input analyzer 150 may convert the user's audio input into text for further processing using any appropriate "speech-to-text" techniques and may extract metadata regarding e.g., people, dates, events, and issues that are the subject of the user's input, as discussed in further detail hereinabove. In the example of FIG. 2A, the input analyzer 150 may extract (as discussed above) metadata indicating that the user is concerned about the behavior (the issue) of their significant other Peter (person involved). The input analyzer 150 may also extract metadata indicating the emotional state of the user by analyzing the audio input signals of the user's response (as discussed above) and determining, based on e.g., the pitch and volume of the user's voice, as well as the user's pause during their reply, that they are concerned/anxious as well as depressed about the situation. The input analyzer 150 may enrich the text of the user's response with this metadata and transmit the enriched text to the state machine 155.

Figure 2B:
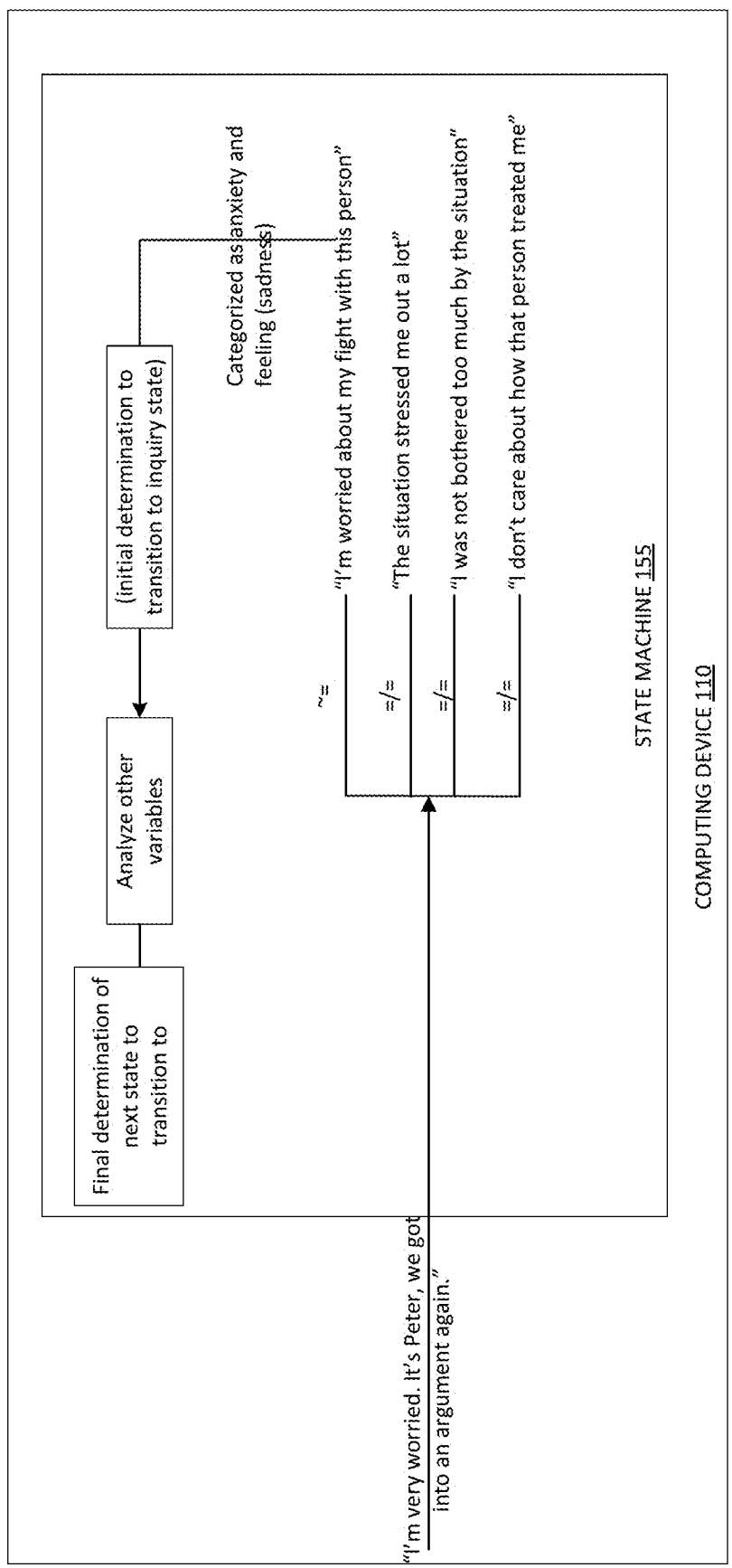
FIG. 2B is a block diagram illustrating comparison of a user's response to a database of well-known sentences, in accordance with some embodiments of the present disclosure.

The classifier ML model 155A of the state machine 155 may analyze the user's response of "I'm very worried. It's Peter, we got into an argument again" based on the well-known user responses/sentences it was trained with as shown in FIG. 2B, and classify the user's response during the first iteration as anxious and feeling (sadness). For example, the classification ML model 155A may determine that the user's response most closely matches the well-known sentence "I'm worried about my fight with this person," and (in some embodiments) account for the volume and tone of the user's voice as well as other metadata extracted from the user's response and determine that the appropriate classification(s) are anxiety and feeling (sadness). The state transition module 155B may determine that the classification(s) are anxiety and feeling (sadness) indicates that more information is required to determine the cause of the anger, and that the inquiry state would be appropriate. The state transition module 155B may also access previous user session information from the user's profile within the database 131 and determine that the user has had arguments with Peter in the past and that more information would assist in determining if the current argument with Peter is indeed related to/similar to the previous arguments with Peter. Thus, the state machine 155 may determine that it should transition to the inquiry state for the next iteration as the other variables support a determination of the inquiry state as the next state to transition to. The state machine 155 may save the metadata extracted from the user's response to the prompt of the initial state (first iteration) in their user profile within database 131.

It should be noted that although the state machine 155 determines that the inquiry state would be appropriate, in some embodiments where a single user response classified as anxious may trigger an anxiety reduction state, the state machine 155 may instead determine that a reassurance/anxiety reduction state is more appropriate given that the user's response has also been classified as anxious. However, in the example of FIG. 2A, the state machine 155 may determine that it is more appropriate to wait until user responses from a threshold number of further iterations of the user session are classified as anxious before triggering an anxiety reduction state transition.

Referring back to FIG. 2A, the state machine 155 may transition to the inquiry state and the second iteration may begin with the state machine 155 outputting the prompt associated with the inquiry state to the output composer 160 along with the extracted metadata and information from the user profile. The base prompt of the inquiry state may comprise the statement "tell me more about what happened." Based on the metadata extracted from the user's response during the first iteration, and information from the user profile, the output composer 160 may modify the base prompt of the inquiry state to recite "this is the third argument you have had, tell me more about what caused the argument." In some embodiments, if the output composer 160 determines that the user is feeling a particular emotion strongly (e.g., sadness or anger), it may further modify the base prompt to include a reassuring phrase. In the example of FIG. 2A, because the output composer 160 has determined from the extracted metadata that the user is sad, it may further modify the base prompt by adding a reassuring sentence (e.g., "its ok to cry") which may result in a modified prompt of "I understand if you want to cry, this is the third argument you have had. Tell me more about what caused the argument." The output composer 160 may then output the modified prompt to the speaker and display of the computing device 110 for presentation to the user via the avatar 350. The user may reply by stating "I believe he doesn't love me anymore so I dumped him."

Once again, the input analyzer 150 may convert the user's audio input into text and may extract metadata therefrom as discussed hereinabove. The input analyzer 150 may enrich the text with the metadata and transmit the enriched text to the state machine 155. The state machine 155 may access the previous user session information from the user's profile within the database 131 and determine that on previous occasions/events, the user has argued with Peter because he is not affectionate or caring enough. The state machine 155 may classify the user's response of "I believe he doesn't love me anymore so I dumped him" during the second iteration as feeling (sadness) and anxiety, and may also examine the user profile to determine that the user is seeking advice on how to deal with the argument emotionally (e.g., based on an indication in the user profile that they previously asked for emotional guidance regarding previous arguments).

Based on the classification of the user's response as feeling (anger) and user profile information indicating that the user is seeking emotional guidance, the state machine 155 may determine that the guidance state would be an appropriate state to transition to. The state machine 155 may save the metadata extracted from the user's response to the prompt of the second iteration in their user profile within database 131 and transition to the guidance state.

The base prompt of the guidance state may be "it's important to make sure you are happy in a relationship," and the third iteration may begin with the state machine 155 outputting the base prompt to the output composer 160 along with the extracted metadata and information from the user profile. Based on the metadata extracted from the user's response during the second iteration, and information from the user profile, the output composer 160 may modify the base prompt of the inquiry state to recite "it's important to make sure you are happy in a relationship, and if Peter is not caring enough then it is difficult to be happy." The output composer 160 may then output the modified prompt to the speaker and display of the computing device 110 for presentation to the user via the avatar 350. The user may reply by stating "I know I can get emotional at times."

Once again, the input analyzer 150 may convert the user's audio input into text and may extract metadata therefrom as discussed hereinabove. The input analyzer 150 may enrich the text with the metadata and transmit the enriched text to the state machine 155. The state machine 155 may access the previous user session information from the user's profile within the database 131 and determine a next state to transition to based thereon. For example, the classification ML model 155A of the state machine 155 may classify the user's response during the third iteration of the user session ("I know I can get emotional at times") as neutral. Based on this classification, along with the other variables discussed hereinabove, the state machine 155 may determine that a second inquiry state is to be transitioned to for the fourth iteration of the user session.

The user session may continue in this way until the user is satisfied with their conversation (e.g., their anxiety has been reduced and/or other goals/objectives of the conversation have been met). The user may indicate this by replying with any appropriate statement such as "thanks for your help" or "I feel better now." In response, the state machine 155 may transition to a user session termination state which may be associated with a base prompt such as e.g., "glad I could be of help . . . see you next time." The state machine 155 may output the base prompt to the output composer 160 which may then output the prompt (either modified or unmodified) to the speaker and display of the computing device 110 for presentation to the user via the avatar 350, thus concluding the final iteration of the user session. It should be noted that the states, metadata, and user profile information discussed herein are exemplary only, and that the interactive wellness application 120A may comprise a number of states, may analyze and extract metadata corresponding to a variety of different information from user responses, and save/store various different aspects of the user's interaction with the interactive wellness application 120A as part of the user profile within database 131.

FIG. 2C illustrates another example of a user session during which the user interacts with the application 120A. In the example of FIG. 2C, the state machine 155 passes the prompt of the initial state to the output composer 160 with no additional information so that it is provided to the user as is.

The user may reply (by speaking into the microphone in the example of FIG. 2A) that "I went to dinner with a friend . . . and I can't believe how they behaved!!!" The input analyzer 150 may convert the user's audio input into text for further processing using any appropriate "speech-to-text" techniques and may extract metadata regarding e.g., people, dates, events, and issues that are the subject of the user's input, as discussed in further detail hereinabove. In the example of FIG. 2A, the input analyzer 150 may extract (as discussed above) metadata indicating that the user is concerned about the behavior (the issue) of a friend (person involved) of the user during a dinner (an event) they attended together. The input analyzer 150 may also extract metadata indicating the emotional state of the user by analyzing the audio input signals of the user's response (as discussed above) and determining, based on e.g., the pitch and volume of the user's voice, as well as the user's pause during their reply, that they are upset/angry about the situation. The input analyzer 150 may enrich the text of the user's response with this metadata and transmit the enriched text to the state machine 155.

Figure 2D:
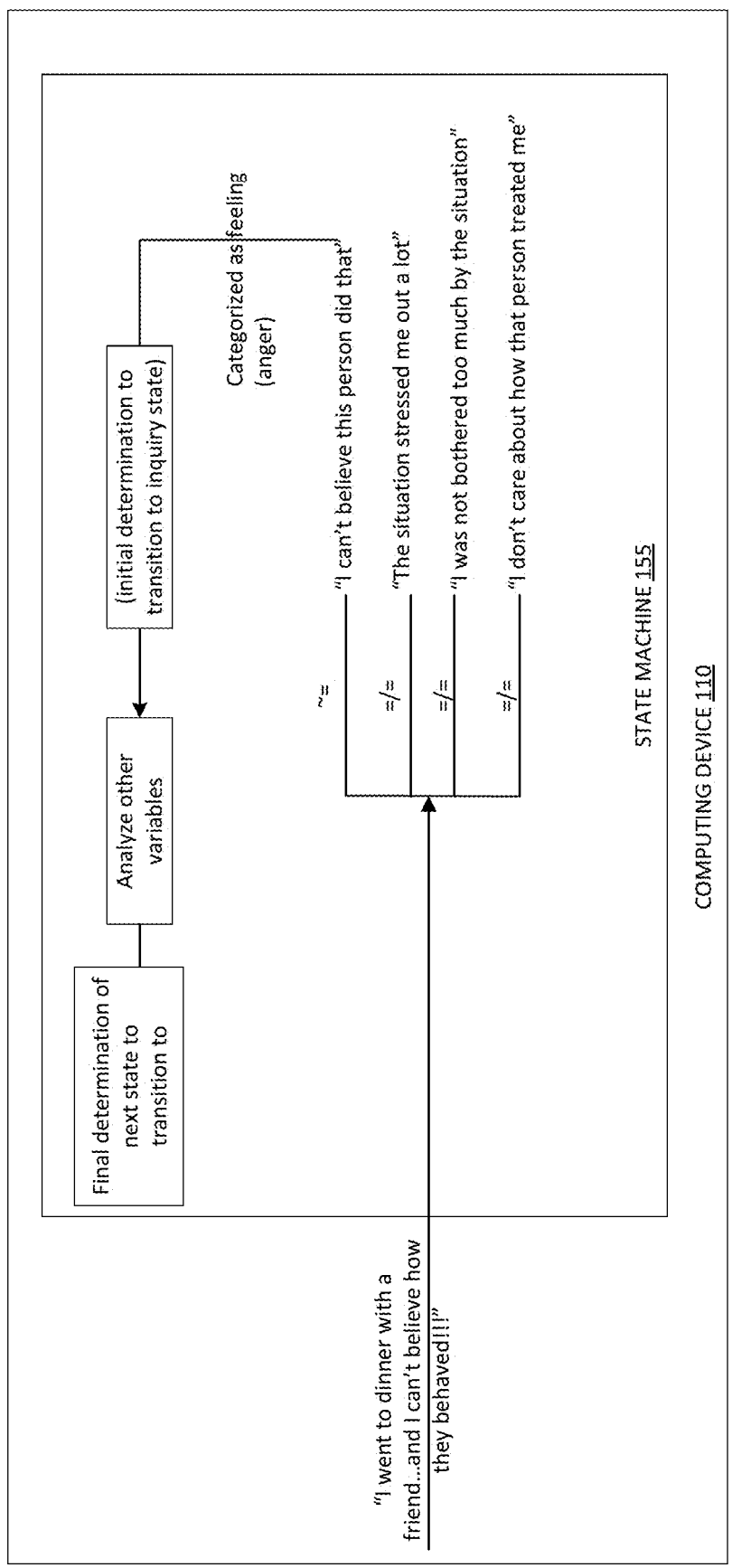
FIG. 2D is a block diagram illustrating comparison of a user's response to a database of well-known sentences, in accordance with some embodiments of the present disclosure.

The classifier ML model 155A of the state machine 155 may analyze the user's response of "I went to dinner with a friend . . . and I can't believe how they behaved!!!" based on the well-known user responses/sentences it was trained with as shown in FIG. 2D, and classify the user's response during the first iteration as feeling (anger). For example, the classification ML model 155A may determine that the user's response most closely matches the well-known sentence "I can't believe this person did that," and (in some embodiments) account for the volume and tone of the user's voice as well as other metadata extracted from the user's response and determine that the appropriate classification is feeling (anger). The state transition module 155B may determine that the classification of feeling (anger) indicates that more information is required to determine the cause of the anger, and that the inquiry state would be appropriate. The state transition module 155B may also access previous user session information from the user's profile within the database 131 and determine that the user has had a similar issue with the friend in the past and that more information would assist in determining if the current issue of the friend's behavior is indeed related to/similar to the previous issues with the friend. Thus, the state machine 155 may determine that it should transition to the inquiry state for the next iteration as the other variables support a determination of the inquiry state as the next state to transition to. The state machine 155 may save the metadata extracted from the user's response to the prompt of the initial state (first iteration) in their user profile within database 131.

Referring back to FIG. 2C, the state machine 155 may transition to the inquiry state and the second iteration may begin with the state machine 155 outputting the prompt associated with the inquiry state to the output composer 160 along with the extracted metadata and information from the user profile. The base prompt of the inquiry state may comprise the statement "tell me more about what happened during the event." Based on the metadata extracted from the user's response during the first iteration, and information from the user profile, the output composer 160 may modify the base prompt of the inquiry state to recite "tell me more about what your friend did during the dinner." In some embodiments, if the output composer 160 determines that the user is feeling a particular emotion strongly (e.g., sadness or anger), it may further modify the base prompt to include a reassuring phrase. For example, if the metadata included with the base prompt indicates that the user is sad, the output composer 160 may append to the base prompt a statement such as "its ok to cry." In the example of FIG. 2C, because the output composer 160 has determined from the extracted metadata that the user is angry, it may further modify the base prompt by adding a reassuring sentence (e.g., "its ok to be angry") which may result in a modified prompt of "its ok to be angry, tell me more about what your friend did during the dinner." The output composer 160 may then output the modified prompt to the speaker and display of the computing device 110 for presentation to the user via the avatar 350. The user may reply by stating "we were having dinner and he had too much to drink again! I really don't know what to do about him."

Once again, the input analyzer 150 may convert the user's audio input into text and may extract metadata therefrom as discussed hereinabove. The input analyzer 150 may enrich the text with the metadata and transmit the enriched text to the state machine 155. The state machine 155 may access the previous user session information from the user's profile within the database 131 and determine that on previous occasions/events, the user has been upset with the friend's behavior after the friend has had too much alcohol to drink. The state machine 155 may classify the user's response of "we were having dinner and he had too much to drink again! I really don't know what to do about him" during the second iteration as feeling (anger) and anxiety, and may also examine the user profile to determine that the user is seeking advice on how to deal with someone (e.g., based on an indication in the user profile that they previously asked for guidance on dealing with this person in a previous similar situation).

Based on the classification of the user's response as feeling (anger) and user profile information indicating that the user is seeking guidance, the state machine 155 may determine that the guidance state would be an appropriate state to transition to. It should be noted that although the state machine 155 determines that the guidance state would be appropriate, in some embodiments where a single user response classified as anxious may trigger an anxiety reduction state, the state machine 155 may instead determine that a reassurance/anxiety reduction state is more appropriate given that the user's response has also been classified as anxious. However, in the example of FIG. 2C, the state machine 155 may determine that it is more appropriate to wait until user responses from a threshold number of further iterations of the user session are classified as anxious before triggering an anxiety reduction state transition. The state machine 155 may save the metadata extracted from the user's response to the prompt of the second iteration in their user profile within database 131 and transition to the guidance state.

The base prompt of the guidance state may be "don't worry, you are not responsible for this action," and the third iteration may begin with the state machine 155 outputting the base prompt to the output composer 160 along with the extracted metadata and information from the user profile. Based on the metadata extracted from the user's response during the second iteration, and information from the user profile, the output composer 160 may modify the base prompt of the inquiry state to recite "don't worry, you are not responsible for your friend's actions, and his drinking is not a reflection on you." The output composer 160 may then output the modified prompt to the speaker and display of the computing device 110 for presentation to the user via the avatar 350. The user may reply by stating "I guess that's true, I still wish there was something I could do to make him realize that his behavior is not good."

Once again, the input analyzer 150 may convert the user's audio input into text and may extract metadata therefrom as discussed hereinabove. The input analyzer 150 may enrich the text with the metadata and transmit the enriched text to the state machine 155. The state machine 155 may access the previous user session information from the user's profile within the database 131 and determine a next state to transition to based thereon. For example, the classification ML model 155A of the state machine 155 may classify the user's response during the third iteration of the user session ("I guess that's true, I still wish there was something I could do to make him realize that his behavior is not good") as neutral. Based on this classification, along with the other variables discussed hereinabove, the state machine 155 may determine that a second inquiry state is to be transitioned to for the fourth iteration of the user session. The base prompt of the second inquiry state may be "why do you think this person takes a particular action?" and the fourth iteration may begin with the state machine 155 outputting the base prompt of the second inquiry state to the output composer 160 along with the extracted metadata from the user's response to the previous prompt and information from the user profile. Based on the metadata extracted from the user's response during the third iteration, and information from the user profile (including the user's response during the first and second iterations), the output composer 160 may modify the base prompt of the inquiry state to recite "why do you think your friend drinks excessively in social situations?" The output composer 160 may then output the modified prompt to the speaker and display of the computing device 110 for presentation to the user via the avatar 350.

The user session may continue in this way until the user is satisfied with their conversation (e.g., their anxiety has been reduced and/or other goals/objectives of the conversation have been met). The user may indicate this by replying with any appropriate statement such as "thanks for your help" or "I feel better now." In response, the state machine 155 may transition to a user session termination state which may be associated with a base prompt such as e.g., "glad I could be of help . . . see you next time."

Figure 3A:
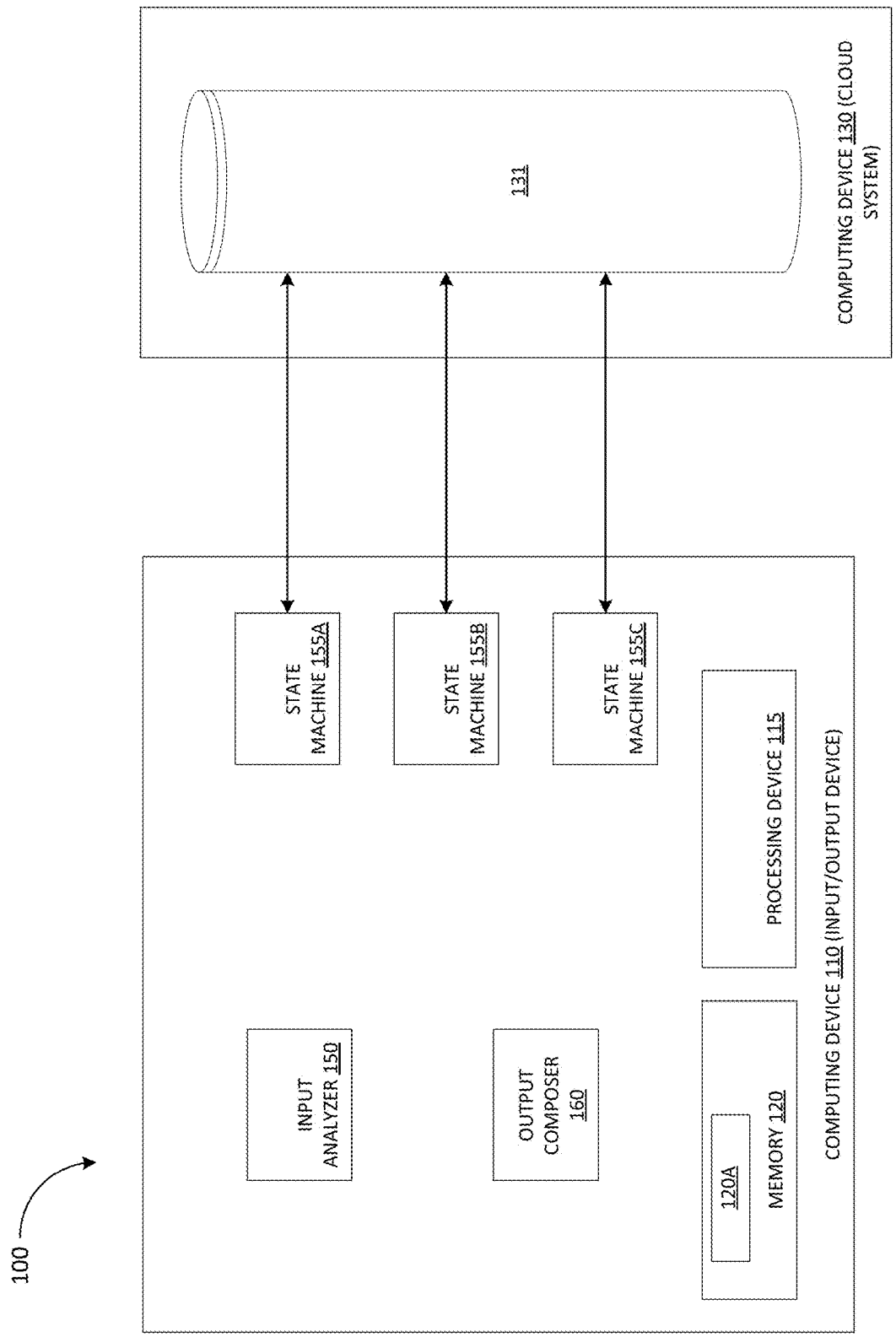
FIG. 3A is a block diagram that illustrates an example system for implementing an interactive conversation application utilizing multiple topic specific state machines, in accordance with some embodiments of the present disclosure.
Figure 3B:
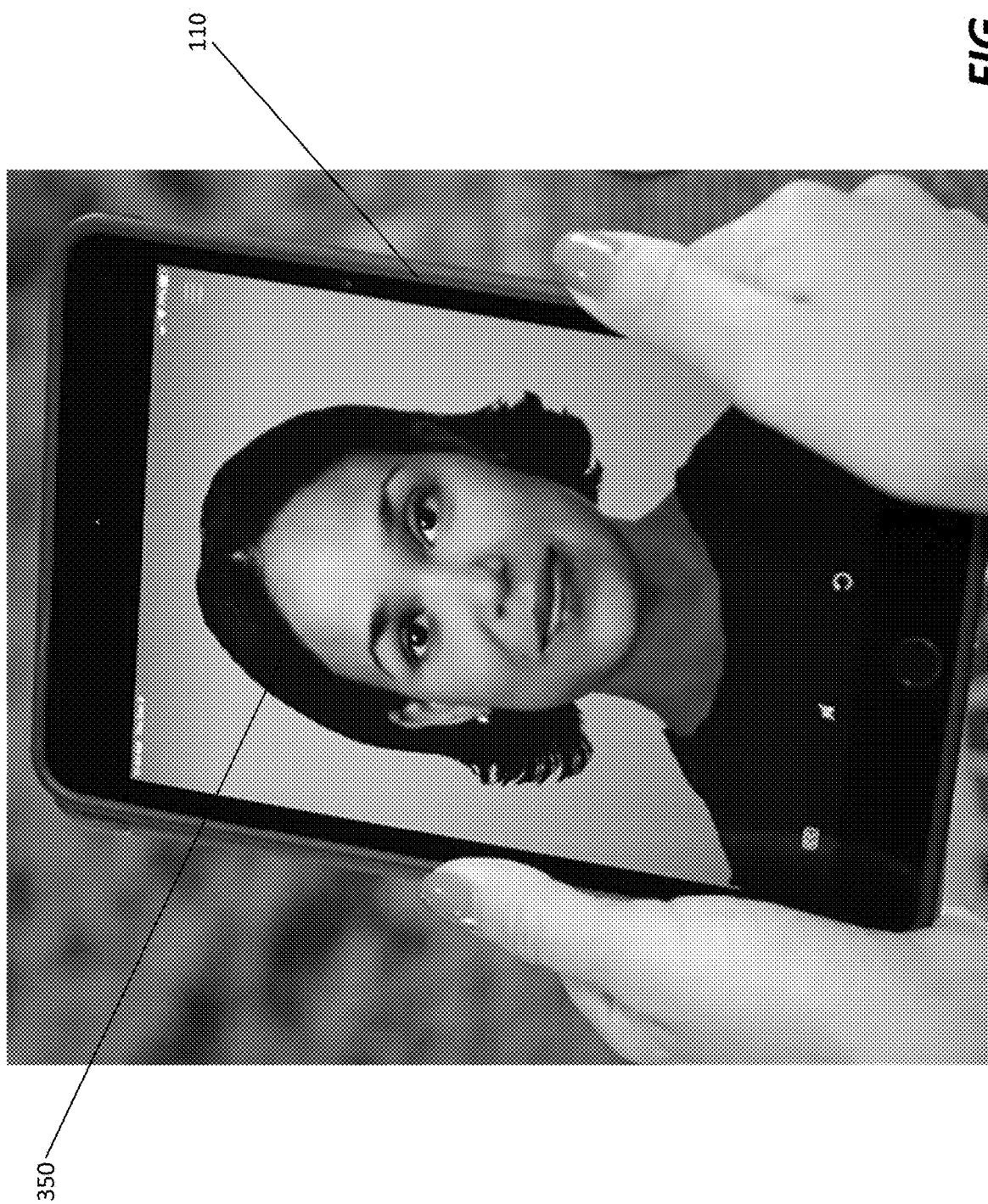
FIG. 3B is a diagram illustrating an avatar via which a user's interaction with the interactive conversation application may be facilitated, in accordance with some embodiments of the present disclosure.

In some embodiments, instead of a single state machine 155, the interactive wellness application 120A may include a set of topic specific state machines 155A-155N as shown in FIG. 3A. Each of the state machines 155A-155N may have states corresponding to a particular topic (work, committed relationships, parenting, etc.) and may be implemented using a dedicated ML model for classifying the user response. As shown in FIG. 3A, the computing device 130 may include a set of databases of well-known sentences 132A-132N, and each topic-specific state machine 155A-155N may have its own dedicated database of well-known sentences 132 that are geared towards the corresponding topic of the state machine. For example, a particular topic specific state machine 155 may correspond to anxiety regulation and may have a database of well-known sentences that are geared towards anxiety regulation.

Upon initializing the interactive wellness application 120A, at the beginning of a user session, the interactive wellness application 120A may provide a way for the user to select a particular topic of interest. For example, the interactive wellness application 120A may provide a UI to the user via the display, where the UI includes a module for selecting between specific topics they wish to address during the user session. Selection of a particular topic in turn may cause the processing device 115 to load a topic-specific state machine 155 corresponding to that topic so that it may establish communication with the input analyzer 150 and the output composer 160. In another example, the user may select a particular topic by vocalizing a topic selection (e.g., via the microphone). At this point, the user's interaction with the interactive wellness application 120A may be as described hereinabove.

In some embodiments, during the course of the user session, the interactive wellness application 120A may determine that the currently selected topic-specific state machine is not appropriate for the user and that a different state machine than the one currently selected by the user should be loaded. For example, if the user initially picked "relationship issues" at the beginning of the user session, but over the course of the user session displays significant anxiety levels (determined as discussed herein), then the interactive wellness application 120A may determine that the relationship issues state machine is not appropriate for the user at the moment. For example, if a threshold number of consecutive user responses are classified as anxious by the currently selected state machine, the interactive wellness application 120A may determine that the relationship issues state machine is not appropriate for the user at the current time because their anxiety issues should be addressed first. In another example, if the user initially picked "relationship issues" at the beginning of the user session, but over the course of the user session the user continuously mentions an issue with their job, then the interactive wellness application 120A may determine that the relationship issues state machine is not appropriate for the user at the current time because their issues with their job should be addressed first.

In some embodiments, the interactive wellness application 120A may use any appropriate method to determine whether a different topic-specific state machine 155 than the one selected by the user should be loaded. For example, the interactive wellness application 120A may utilize a separate ML model, a rule-based algorithm, a set of keywords, or any combination of these techniques.

For example, in some embodiments, the interactive wellness application 120A's determination of whether a different state machine than the one selected by the user should be loaded may be based on a scoring system. The interactive wellness application 120A may determine a state machine transition score based on the detection of certain keywords in user responses and/or an anxiety level of the user. In some embodiments, certain factors may be worth certain "points." For example, when the user expresses pain this may correspond to 1 point, when a change in rate of speech/pace of talking is detected, this may be worth 2 points. When the number of points for each detected factor adds up to a threshold number of points, then the interactive wellness application 120A may determine that the currently selected topic-specific state machine is not appropriate for the user at the current time and may ask the user if they want to switch to different topic or may automatically switch to a different topic as discussed herein.

Upon determining that the currently selected topic-specific state machine 155 is not appropriate, the interactive wellness application 120A may determine a new topic specific state machine 155 for use with the user session based on the user's response during the current state including metadata extracted therefrom by the input analyzer 150, a classification of the user's response during the current state into a particular category among a set of predefined categories (e.g., defense, neutral, feeling, anxiety, as discussed in further detail herein), and data from the user profile including the user's responses from previous iterations/states of the user session as well as previous user sessions including metadata extracted therefrom (e.g., any party the user is/was having issues with, identification of the issues that were/are relevant, how the user is/was feeling). The interactive wellness application 120A may load the determined new topic specific state machine 155 and continue the user session as described hereinabove.

In some embodiments, upon determining that a currently selected topic-specific state machine 155 is not appropriate and determining a new topic specific state machine 155 for use with the user session, the interactive wellness application 120A may automatically load the determined new topic-specific state machine and provide prompts informing the user when such a change has been made. For example, the interactive wellness application 120A (via the avatar 350) may provide a prompt stating "lets address this anxiety you are feeling and get back to your relationship later." In other embodiments, the interactive wellness application 120A may ask the user for permission before loading a different topic-specific state machine 155 than the one currently selected by the user.

FIG. 4A illustrates an example of a machine learning model 400 that could be used in conjunction with some embodiments of the present disclosure. In the example of FIG. 4A, the ML model 400 may comprise a trained CNN ML model that takes input data 402 (e.g., user data) into convolutional layers (aka hidden layers) 403, and applies a series of trained weights or filters 404 to the input data 406 in each of the convolutional layers 403. The output of the first convolutional layer is an activation map (not shown), which is the input to the second convolution layer, to which a trained weight or filter (not shown) is applied, where the output of the subsequent convolutional layers results in activation maps that represent more and more complex features of the input data to the first layer. After each convolutional layer a non-linear layer (not shown) is applied to introduce non-linearity into the problem, which nonlinear layers may include an activation function such as tan h, sigmoid or ReLU. In some cases, a pooling layer (not shown) may be applied after the nonlinear layers, also referred to as a downsampling layer, which basically takes a filter and stride of the same length and applies it to the input, and outputs the maximum number in every sub-region the filter convolves around. Other options for pooling are average pooling and L2-norm pooling. The pooling layer reduces the spatial dimension of the input volume reducing computational costs and to control overfitting. The final layer(s) of the network is a fully connected layer, which takes the output of the last convolutional layer and outputs an n-dimensional output vector representing the quantity to be predicted, e.g., a classification of the user's response. This may result in predictive output 406 (O*). The trained weights 404 may be different for each of the convolutional layers 403, as will be described more fully below.

To achieve this real-world prediction/detection, a neural network needs to be trained on known data inputs or training examples resulting in trained CNN 408. To train CNN 400, many different training examples (e.g., user data including prompts, responses from previous user conversations that have been labeled with their classifications/emotional content) are input into the model. A skilled artisan in neural networks will fully understand the description above provides a somewhat simplistic view of CNNs to provide some context for the present discussion and will fully appreciate the application of any CNN alone or in combination with other neural networks or other entirely different machine learning models will be equally applicable and within the scope of some embodiments described herein.

Figure 4B:
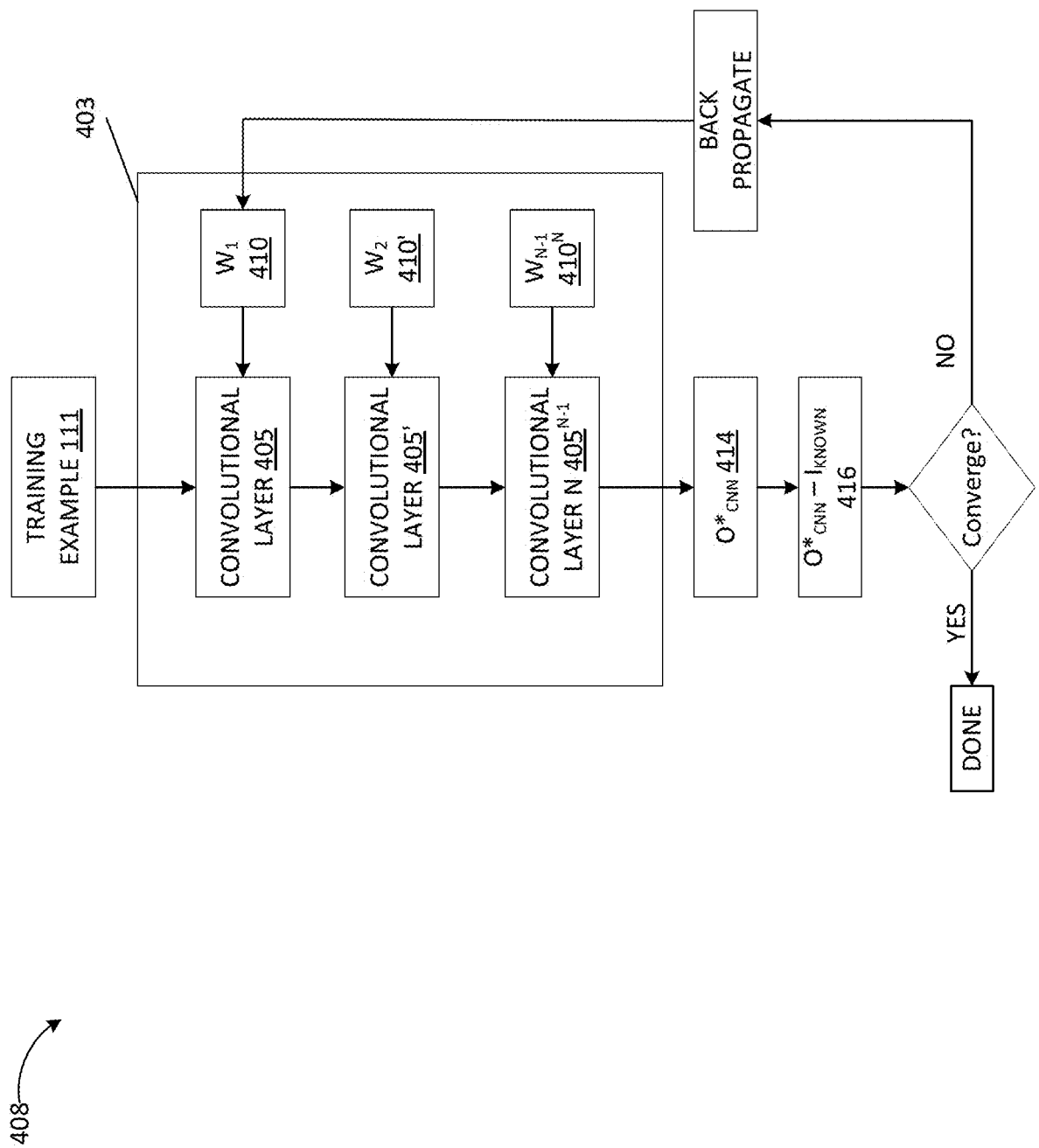
FIG. 4B is a diagram illustrating the training of a machine learning model.

FIG. 4B demonstrates training CNN 408. In FIG. 4B convolutional layers 403 are shown as individual hidden convolutional layers 405, 405' to convolutional layer (405)' and the final nth layer is a fully connected layer. It will be appreciated that last layers may be more than one fully connected layer. Training example 411 is input into convolutional layers 403, a nonlinear activation function (not shown) and weights 410, 410' through 410n are applied to training example 411 in series, where the output of any hidden layer is input to the next layer, and so on until the final nth fully connected layer $(405)^{n-1}$ produces output 414. Output or prediction 414 (*) is compared against training example 411 (e.g., labeled user data) resulting in a difference 416 between output or prediction 414 and training example 411 (also shown as $I_{known}$ in FIG. 4B). If the difference or loss 416 is less than some preset loss (e.g., output or prediction 414 predicts the correct class for a user's response), the CNN is converged and considered trained. If the CNN has not converged, using the technique of back-propagation, weights 410 and 410' through 410' are updated in accordance with how close the prediction is to the known input. The skilled artisan will appreciate that methods other than back propagation may be used to adjust the weights. The second training example (e.g., different user data) is input and the process is repeated again with the updated weights, which are then updated again and so on until the nth training example (e.g., nth user data) has been input. This is repeated over and over with the same n-training examples until the convolutional neural network (CNN) 400 is trained or converges on the correct outputs for the known inputs. Once CNN 408 is trained, weights 410, 410' through 410' are fixed and used in trained CNN 400, which are weights 404 as depicted in FIG. 4B. As explained, there are different weights for each convolutional layer 403 and for each of the fully connected layers. The trained CNN 400 or model is then fed user data to determine or predict that which it is trained to predict/identify (e.g., predict the correct classification for a user's response), as described above. Any trained model, Transformers, CNN, RNN, etc. may be trained further, i.e., modification of the weights may be permitted, with additional training examples or with predicted data output by the model which is then used as a training example. The machine learning model can be trained "offline", e.g., trained once on a computational platform separate from the platform using/executing the trained model, and then transferred to that platform. Alternatively, embodiments described herein may periodically or continually update the machine learning model based on newly acquired training data. This updated training may occur on a separate computational platform which delivers the updated trained models to the platform using/executing the re-trained model over a network connection, or the training/re-training/update process may occur on the platform itself as new data is acquired. The skilled artisan will appreciate the CNN is applicable to data in a fixed array (e.g., a picture, character, word etc.) or a time sequence of data.

Figure 5A:
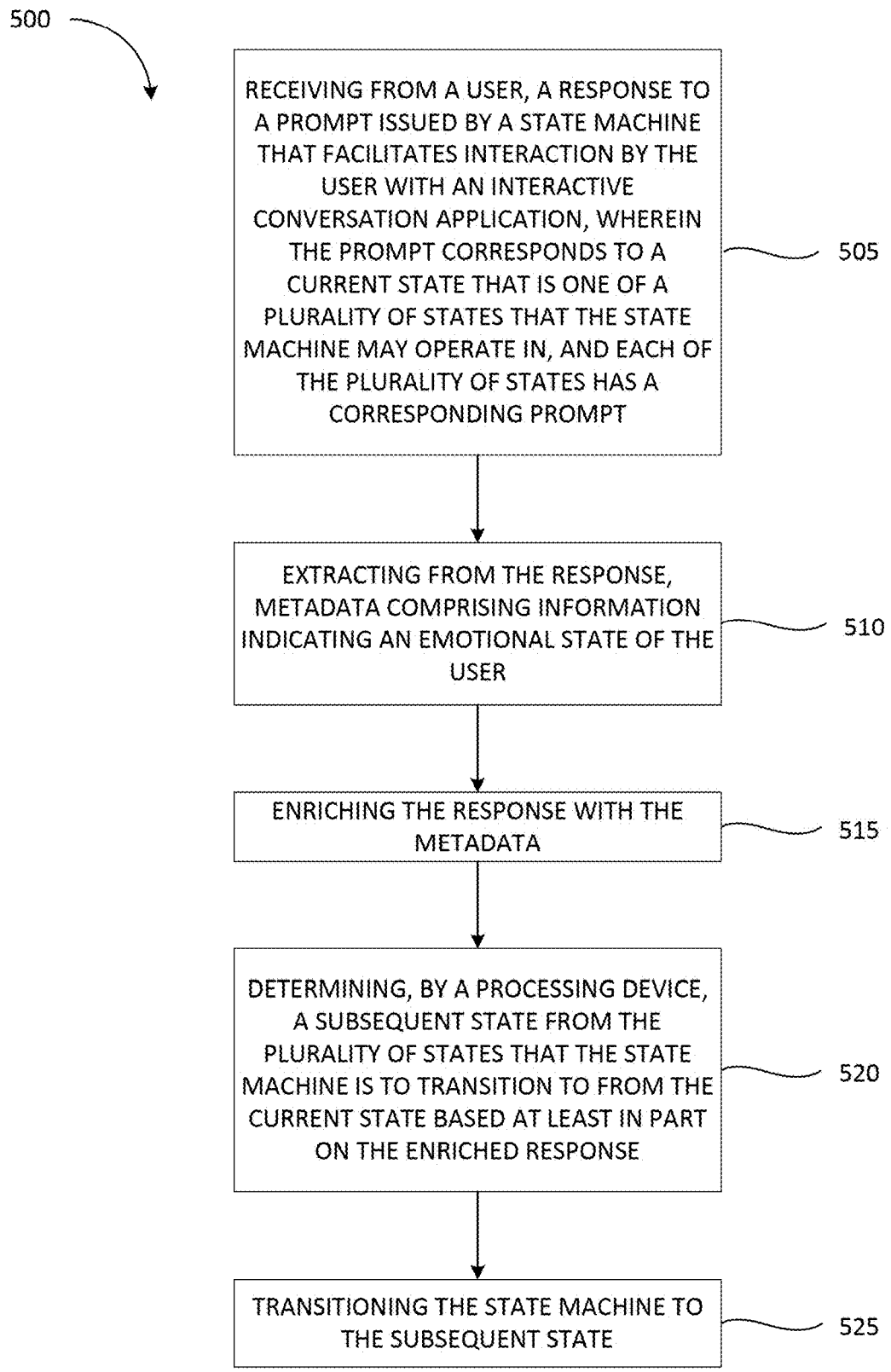
FIG. 5A is a flow diagram of a method for implementing an interactive conversation platform that can engage in conversation with a user in a manner that simulates humanistic interaction including emotion recognition and learned understanding of users, in accordance with some embodiments of the present disclosure.

FIG. 5A is a flow diagram of a method 500 for implementing an interactive conversation platform that can engage in conversation with a user in a manner that simulates humanistic interaction including emotion recognition and learned understanding of users, in accordance with some embodiments of the present disclosure. Method 500 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 500 may be performed by a computing device (e.g., computing device 110 illustrated in FIG. 1B).

The user's interaction with the interactive wellness application 120A (hereinafter referred to as the user session) may be an iterative process, where each iteration is defined by a prompt provided to the user by the interactive wellness application 120A and a user's response thereto. More specifically, the prompt provided to the user by the interactive wellness application 120A at each iteration may be based on a state (from among a plurality of states) that the state machine 155 is in during that iteration. Each of the plurality of states may be associated with a particular predefined prompt (e.g., sentence(s)/statement(s), question(s)) that can be output by the state machine 155 upon the state machine 155 transitioning to that state. The state machine 155 may transition through a number of different states over the course of a user session, where each different state represents a particular objective that the interactive wellness application 120A is to accomplish during an iteration (e.g., reducing the user's anxiety, or obtaining more information about an issue that is causing the user anxiety). The predefined prompt associated with a state may be a base prompt geared towards accomplishing the state's objective and can be modified by the output composer 160 (i.e., further tailored to the user by the output composer 160 as discussed in further detail herein) based on a number of factors before being output to the user, as discussed in further detail herein.

At block 505, in response to a prompt by the wellness application 120A (e.g., delivered via the avatar 350) during a current state, the user may vocalize their response to the prompts by speaking into the microphone or typing their response on the keyboard. A prompt as used herein may comprise one or more statements and/or questions designed to engage the user in discussion about a topic(s) of relevance. When analyzing an audio/spoken input from the user, the input analyzer 150 may convert the audio input into text for further processing using any appropriate "speech-to-text" techniques. In some embodiments, the input analyzer 150 may utilize on-board speech-to-text capabilities of the computing device 110, while in other embodiments the input analyzer 150 may utilize a remote service such as the AWS' speech-to-text service (which may be running e.g., on the computing device 130).

At block 510, the input analyzer 150 may analyze the text of user response (whether typed by the user or generated as a result of speech-to-text processing) to extract metadata comprising information relevant to the user from the text. The input analyzer 150 may extract metadata regarding e.g., people, dates, events, and issues that are the subject of the user's input and at block 515, may enrich the text of their response with this metadata. The input analyzer 150 may comprise any appropriate machine learning (ML) algorithm(s) such as natural language processing algorithms and/or neural networks to extract the metadata (relevant information) from the text of the user's response. For instance, the input analyzer 150 may utilize the named entity recognition class of algorithms to extract relevant entities from the text of the user's response. In another example, the input analyzer 150 may leverage any suitable pattern matching algorithm to look for specific key words/phrases or a specific set of key words/phrases from the text of the user's response.

In some embodiments, when the user has provided their responses to prompts from the application 120A by speaking into the microphone, the input analyzer 150 may also analyze the captured audio signals corresponding to the user's response to extract metadata indicating the emotional state of the user. The processing device 115 (via the input analyzer 150) may perform this analysis using any (or a combination) of several audio analysis techniques. For example, the input analyzer 150 may perform a static analysis of audio frequencies of the user's response, e.g., to determine whether the user is crying or upset. In another example, the input analyzer 150 may also utilize one or more neural networks that are trained to detect emotions from audio signals by analyzing physical indicators of the user's emotional state such as the pitch, tone, and words per minute of the user's response, in addition to other features such as tendency to stop talking/pauses in speech, and a decrease or increase in volume as the user provides their response. The input analyzer 150 may generate one or more emotional indicators (e.g., happy, sad, angry, crying etc.) of the user's emotional state based on the physical indicators of the user's emotional state and add these emotional indicators along with the physical indicators of the user's emotional state to the response metadata that is extracted from the text of the user's response In addition, if the user has provided his input via camera (as well as via microphone and/or keyboard), the input analyzer 150 may analyze video frames of the user's face/body captured by the camera during their response to extract additional metadata indicating the user's emotional state. For example, the input analyzer 150 may utilize one or more neural networks to analyze muscle movements, facial expressions, so-called facial landmarks, whether the user is facing the camera or looking away, and the user's posture (sitting/standing, shoulders hunched etc.), among other physical indicators indicating the user's emotional state. Such physical indicators may also be used to determine other characteristics of a person (i.e., gender, age, etc.). The input analyzer 150 may generate (accounting for physical indicators extracted from the captured audio signals as well) one or more emotional indicators (e.g., happy, sad, angry, crying etc.) of the user's emotional state and add these emotional indicators along with the physical indicators of the user's emotional state to the response metadata that is extracted from the text of the user's response. As discussed in further detail herein, the response metadata may enable the interactive wellness application 120A to "humanize" its interaction with the user by allowing it to account for factors such as the current emotional state of the user, previous interactions with the user, and other information when determining a next prompt to output to the user (as discussed in further detail herein). The input analyzer 150 may utilize a separate neural network (from the one used to extract response metadata from the text of the user's response) for analysis of the physical indicators, and in some embodiments, may utilize a separate neural network for analyzing each of the physical indicators.

At block 520, based on the user's response (processed and enriched by the input analyzer 150) to the prompt of the current state and other factors (as described in further detail herein), the state machine 155 may determine a state it should transition to during the next iteration of the user session (or determine that it should remain in the current state during the next iteration of the user session). To determine the next state to transition to during the user session, the state machine 155 may consider several variables, including but not limited to the previous state of the user session (if any), the user's response including metadata extracted therefrom by the input analyzer 150 during the current state, the user's responses from previous iterations/states of the user session as well as previous user sessions including metadata extracted therefrom (e.g., any party the user is/was having issues with, identification of the issues that were/are relevant, how the user is/was feeling), and a classification of the user response during the current state into one of a set of predetermined categories. The state machine 155 may comprise a classification ML model 155A to perform the classification of the user response, and may comprise a state transition module 155B to determine a next state to transition to based on the variables described hereinabove (or a subset thereof) as discussed in further detail hereinabove.

At block 525, upon determining a new state to transition to, the state machine 155 may save the metadata extracted from the user's response to the prompt of the current state in their user profile within database 131 and then transition to the new state. The state machine 155 may pass the predefined prompt corresponding to the new state (which may be the same as the current state) to the output composer 160, together with the user profile including user responses and metadata that were extracted from previous iterations of the user session and previous user sessions (thus, signaling the beginning of a new iteration of the user session). The prompt corresponding to a state may comprise a base structure that can be modified with user specific words/phrases based on the aggregated information from the current iteration as well as information from the user profile. The output composer 160 may leverage all the information received from the state machine 155 to craft the appropriate response to return to the user (by modifying the base prompt of the new state the state machine 155 is transitioning to), and may output the response through the avatar 350 displayed on the display of computing device 110. The output composer 160 may be executed either within the computing device 110 as shown in FIG. 1B or remotely, for instance through a cloud-based infrastructure the computing device 110 communicates with (e.g., computing device 130), or as a mix of both.

In this way, the state machine 155 may engage in an iterative process where the user's responses to prompts (and associated metadata) at each state are analyzed in the same way by the state machine 155 and this data is aggregated (in the database 131) throughout the iterations and is used continuously by the state machine 155 to inform state transition decisions (i.e., what kinds prompts to output) at future iterations of the user session.

Figure 5B:
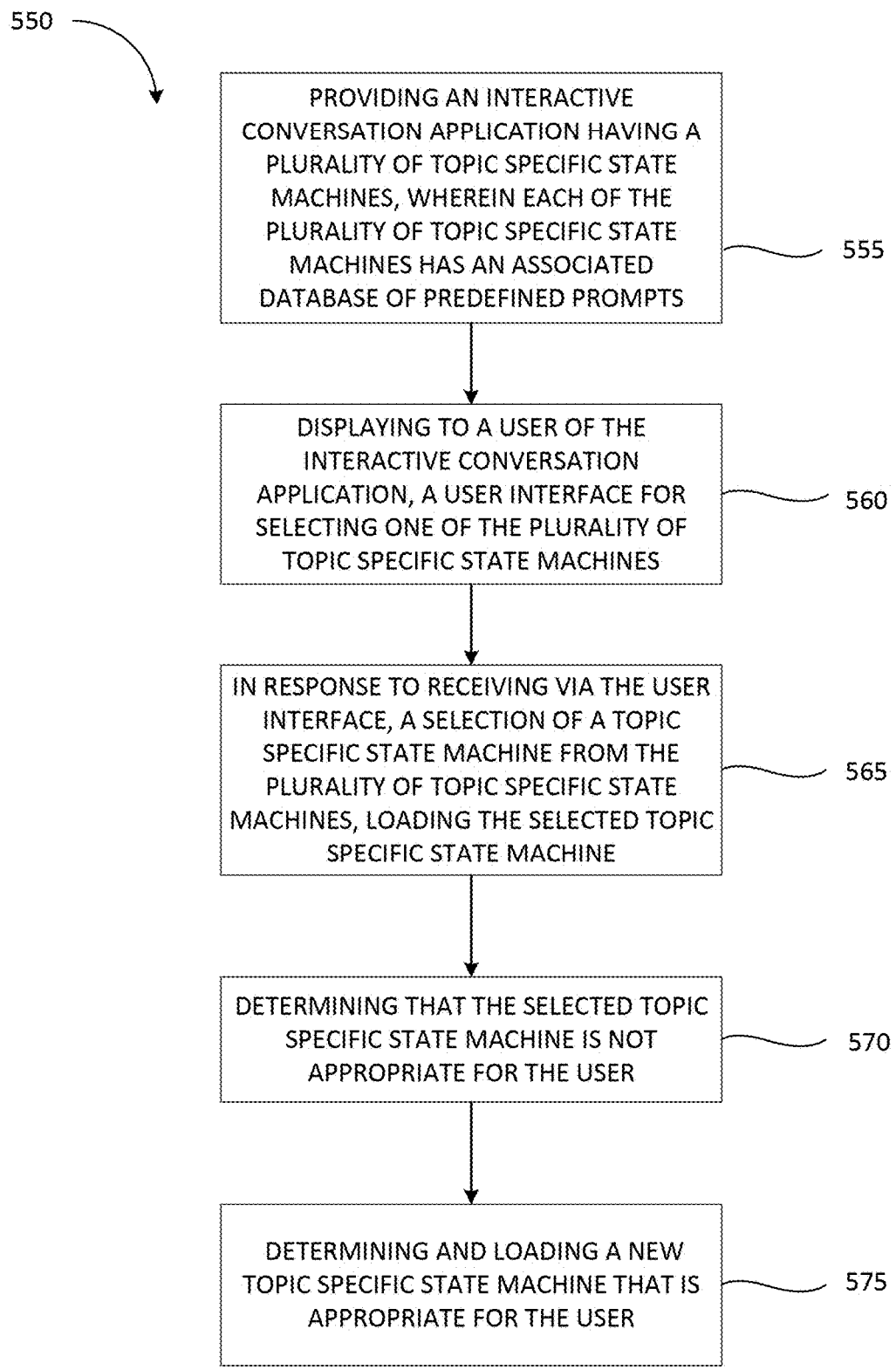
FIG. 5B is a flow diagram of a method for implementing an interactive conversation platform that can engage in conversation with a user in a manner that simulates humanistic interaction utilizing multiple topic specific state machines, in accordance with some embodiments of the present disclosure.

FIG. 5B is a flow diagram of a method 550 for implementing an interactive conversation platform that utilizes a plurality of topic specific state machines for engaging in conversation with a user in a manner that simulates humanistic interaction, in accordance with some embodiments of the present disclosure. Method 550 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof in some embodiments, the method 550 may be performed by a computing device (e.g., computing device 110 illustrated in FIG. 3A).

In some embodiments, instead of a single state machine 155, at block 555 the interactive wellness application 120A may include a set of topic specific state machines 155A-155N as shown in FIG. 3A. Each of the state machines 155A-155N may have states corresponding to a particular topic work, committed relationships, parenting, etc. and may be implemented using a dedicated ML model. As shown in FIG. 3A, the computing device 130 may include a set of databases of well-known sentences 132A-132N, and each state machine 155A-155N may have its own dedicated database of well-known sentences 132 that are geared towards the corresponding topic of the state machine.

Upon initializing the interactive wellness application 120A, at the beginning of a user session, at block 560, the interactive wellness application 120A may provide a provide a way for the user to select a particular topic of interest. For example, the interactive wellness application 120A may provide a UI to the user via the display, where the UI includes a module for selecting between specific topics they wish to address during the user session. Selection of a particular topic in turn may cause the processing device 115 to load the specific state machine 155 corresponding to that topic so that it may establish communication with the input analyzer 150 and the output composer 160. In another example, the user may select a particular topic by vocalizing a topic selection (e.g., via the microphone). At block 565, selection of a particular topic in turn may cause the processing device 115 to load the specific state machine corresponding to that topic so that it may establish communication with the input analyzer 150 and the output composer 160. At this point, the user's interaction with the interactive wellness application 120A may be as described hereinabove.

In some embodiments, during the course of the user session, at block 570, the interactive wellness application 120A may determine that the currently selected topic-specific state machine is not appropriate for the user and that a different state machine than the one currently selected by the user should be loaded. For example, if the user initially picked "relationship issues" at the beginning of the user session, but over the course of the user session displays significant anxiety levels (determined as discussed herein), then the interactive wellness application 120A may determine that the relationship issues state machine is not appropriate for the user at the moment. For example, if a threshold number of consecutive user responses are classified as anxious by the currently selected state machine, the interactive wellness application 120A may determine that the relationship issues state machine is not appropriate for the user at the current time because their anxiety issues should be addressed first. In another example, if the user initially picked "relationship issues" at the beginning of the user session, but over the course of the use session the user continuously mentions an issue with their job, then the interactive wellness application 120A may determine that the relationship issues state machine is not appropriate for the user at the current time because their issues with their job should be addressed first.

In some embodiments, the interactive wellness application 120A may use any appropriate method to determine whether a different topic-specific state machine 155 than the one selected by the user should be loaded. For example, the interactive wellness application 120A may utilize a separate ML model, a rule-based algorithm, a set of keywords, or any combination of these techniques.

For example, in some embodiments, the interactive wellness application 120A's determination of whether a different state machine than the one selected by the user should be loaded may be based on a scoring system. The interactive wellness application 120A may determine a state machine transition score based on the detection of certain keywords in user responses and/or an anxiety level of the user. In some embodiments, certain factors may be worth certain "points." For example, when the user expresses pain this may correspond to 1 point, when a change in rate of speech/pace of talking is detected, this may be worth 2 points. When the number of points for each detected factor adds up to a threshold number of points, then the interactive wellness application 120A may determine that the currently selected topic-specific state machine is not appropriate for the user and may ask the user if they want to switch to different topic. The interactive wellness application 120A may determine whether a different topic-specific state machine 155 than the one selected by the user should be loaded by utilizing a separate ML model, a rule-based algorithm, a set of keywords, or any combination of these techniques.

At block 575, upon determining that the currently selected topic-specific state machine 155 is not appropriate, the interactive wellness application 120A may determine a new topic specific state machine 155 for use with the user session based on one or more of: the user's response during the current state including metadata extracted therefrom by the input analyzer 150, the classification of the user's response during the current state into a particular category among the set of predefined categories (e.g., defense, neutral, feeling, anxiety, as discussed in further detail herein), and data from the user profile including the user's responses from previous iterations/states of the user session as well as previous user sessions including metadata extracted therefrom (e.g., any party the user is/was having issues with, identification of the issues that were/are relevant, how the user is/was feeling). The interactive wellness application 120A may load the determined new topic specific state machine 155 and continue the user session as described hereinabove.

In some embodiments, upon determining that a currently selected topic-specific state machine 155 is not appropriate and determining a new topic specific state machine 155 for use with the user session, the interactive wellness application 120A may automatically load the determined new topic-specific state machine and provide prompts informing the user when such a change has been made. For example, the interactive wellness application 120A (via the avatar 350) may provide a prompt stating "lets address this anxiety you are feeling and get back to your relationship later." In some embodiments, the interactive wellness application 120A may ask the user for permission before loading a different topic-specific state machine 155 than the one currently selected by the user.

Figure 6:
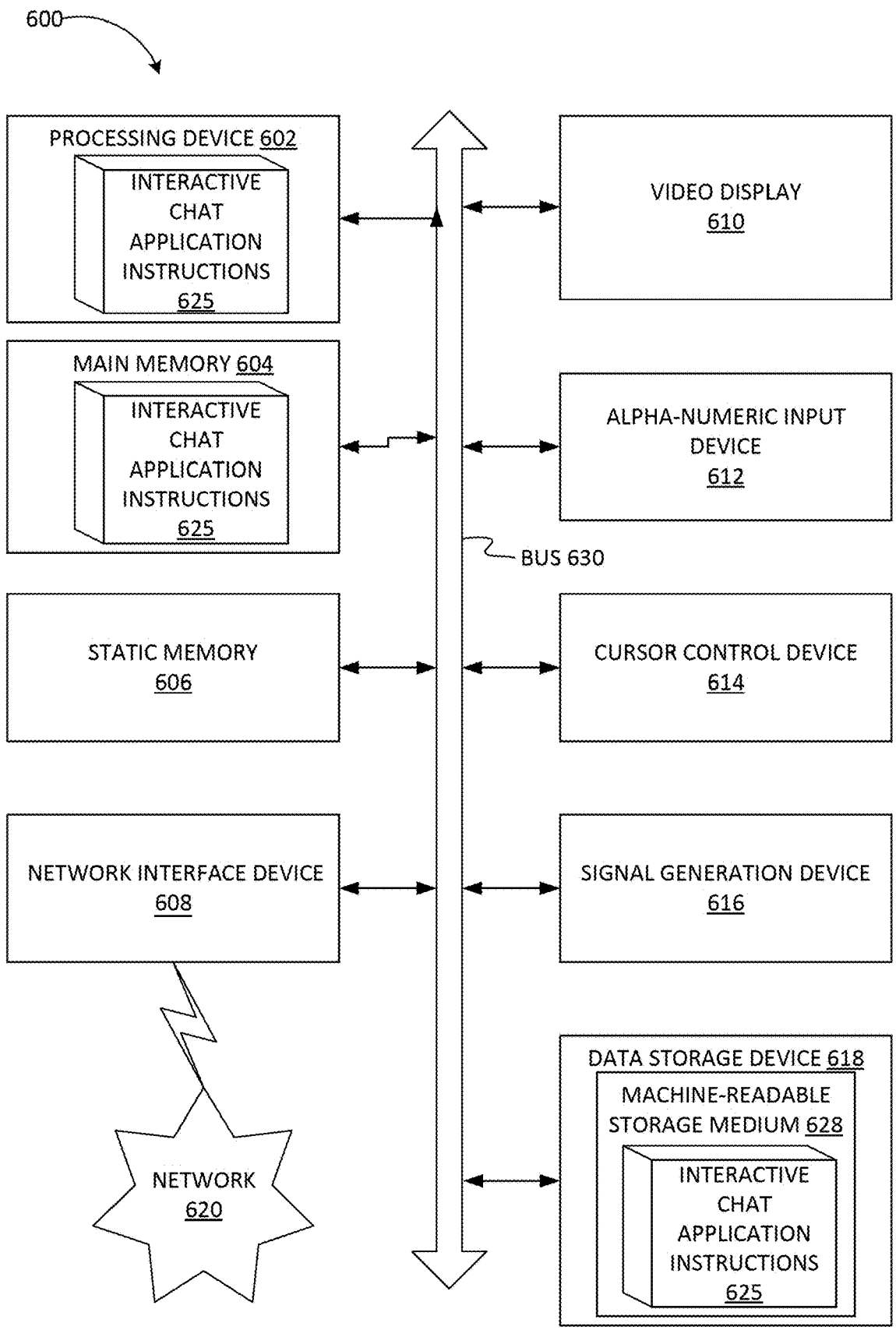
FIG. 6 is a block diagram of an example computing device that may perform one or more of the operations described herein, in accordance with some embodiments of the present disclosure.

FIG. 6 illustrates a diagrammatic representation of a machine in the example form of a computer system 600 within which a set of instructions, for causing the machine to perform any one or more of the methodologies discussed herein for implementing an interactive conversation platform that can engage in conversation with a user in a manner that simulates humanistic interaction including emotion recognition and learned understanding of users.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 600 may be representative of a server.

The exemplary computer system 600 includes a processing device 602, a main memory 604 (e.g., read-only memory (ROM), flash memory, dynamic random access memory (DRAM), a static memory 606 (e.g., flash memory, static random access memory (SRAM), etc.), and a data storage device 618 which communicate with each other via a bus 630. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Processing device 602 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute interactive chat application instructions 625, for performing the operations and steps discussed herein.

The data storage device 618 may include a machine-readable storage medium 628, on which is stored one or more sets of interactive chat application instructions 625 (e.g., software) embodying any one or more of the methodologies of functions described herein. The interactive chat application instructions 625 may also reside, completely or at least partially, within the main memory 604 or within the processing device 602 during execution thereof by the computer system 600; the main memory 604 and the processing device 602 also constituting machine-readable storage media. The interactive chat application instructions 625 may further be transmitted or received over a network 620 via the network interface device 608.

The machine-readable storage medium 628 may also be used to store instructions to perform a method for determining if a controller that can service a CRD exists, as described herein. While the machine-readable storage medium 628 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Unless specifically stated otherwise, terms such as "receiving," "routing," "updating," "providing," or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general purpose computing device selectively programmed by a computer program stored in the computing device. Such a computer program may be stored in a computer-readable non-transitory storage medium.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method comprising:
   iteratively:
   receiving from a user, a response to a prompt issued by a state machine that facilitates interaction by the user with an interactive conversation application, wherein the prompt corresponds to a current state that is one of a plurality of states that the state machine may operate in, and each of the plurality of states corresponds to a conversational objective to be achieved when the state is transitioned to and comprises a corresponding prompt;
   extracting from the response, metadata including an emotional state of the user, wherein the emotional state of the user corresponds to feelings that the user is experiencing as a result of one or more issues that the user is discussing with the interactive conversation application;
   enriching the response with the metadata;
   determining, by a processing device a subsequent state from the plurality of states that the state machine is to transition to from the current state based at least in part on the enriched response and the metadata; and
   transitioning the state machine to the subsequent state by:
   modifying a prompt corresponding to the subsequent state based on the enriched response, responses by the user to prompts corresponding to previous states of the state machine, and metadata extracted from the responses by the user to prompts corresponding to previous states of the state machine, wherein the modified prompt includes information from the responses by the user to prompts corresponding to previous states of the state machine; and outputting the modified prompt to the user.

2. The method of claim 1 further comprising:

adding the metadata to a user database comprising metadata extracted from the responses by the user to prompts corresponding to previous states of the state machine.

3. The method of claim 2, wherein the metadata further indicates people, dates, events, and issues that are subjects of the response.

4. The method of claim 2, wherein determining the subsequent state that the state machine is to transition to comprises:

classifying the enriched response; and determining the subsequent state that the state machine is to transition to based on the classification of the enriched response.

5. The method of claim 2, wherein the subsequent state that the state machine is to transition to is determined based further on a previous state of the state machine.

6. The method of claim 2, wherein the subsequent state that the state machine is to transition to is determined based further on the responses by the user to prompts corresponding to previous states of the state machine.

7. The method of claim 2, wherein the subsequent state that the state machine is to transition to is determined based further on the metadata extracted from the responses by the user to prompts corresponding to previous states of the state machine.

8. The method of claim 1, wherein the response comprises one or more of audio data, text data, and video data.

9. The method of claim 8, further comprising:

analyzing the audio and video data of the response to extract physical indicators of an emotional state of the user; and adding the physical indicators to the metadata.

10. The method of claim 9 wherein the physical indicators comprise one or more of: pitch, tone, words per minute, pauses in speech, and changes in volume.

11. A system comprising:

a memory; and a processing device operatively coupled to the memory, the processing device to:

iteratively:

receive from a user, a response to a prompt issued by a state machine that facilitates interaction by the user with an interactive conversation application, wherein the prompt corresponds to a current state that is one of a plurality of states that the state machine may operate in, and each of the plurality of states corresponds to a conversational objective to be achieved when the state is transitioned to and comprises a corresponding prompt;

extract from the response, metadata including an emotional state of the user, wherein the emotional state of the user corresponds to feelings that the user is experiencing as a result of one or more issues that the user is discussing with the interactive conversation application;

enrich the response with the metadata;

determine a subsequent state from the plurality of states that the state machine is to transition to from the current state based at least in part on the enriched response and the metadata; and transition the state machine to the subsequent state by:

modifying a prompt corresponding to the subsequent state based on the enriched response, responses by the user to prompts corresponding to previous states of the state machine, and metadata extracted from the responses by the user to prompts corresponding to previous states of the state machine, wherein the modified prompt includes information from the responses by the user to prompts corresponding to previous states of the state machine; and outputting the modified prompt to the user.

12. The system of claim 11, wherein the processing device is further to:

add the metadata to a user database comprising metadata extracted from the responses by the user to prompts corresponding to previous states of the state machine.

13. The system of claim 12, wherein the metadata further indicates people, dates, events, and issues that are subjects of the response.

14. The system of claim 12, wherein to determine the subsequent state that the state machine is to transition to, the processing device is to:

classify the enriched response; and determine the subsequent state that the state machine is to transition to based on the classification of the enriched response.

15. The system of claim 12, wherein the processing device determines the subsequent state that the state machine is to transition to based further on a previous state of the state machine.

16. The system of claim 12, wherein the processing device determines the subsequent state that the state machine is to transition to based further on the responses by the user to prompts corresponding to previous states of the state machine.

17. The system of claim 12, wherein the processing device determines the subsequent state that the state machine is to transition to based further on the metadata extracted from the responses by the user to prompts corresponding to previous states of the state machine.

18. The system of claim 11, wherein the response comprises one or more of audio data, text data, and video data.

19. The system of claim 18, wherein the processing device is further to:

analyze the audio and video data of the response to extract physical indicators of an emotional state of the user; and add the physical indicators to the metadata.

20. The system of claim 19, wherein the physical indicators comprise one or more of: pitch, tone, words per minute, pauses in speech, and changes in volume.

21. A non-transitory computer-readable medium having instructions stored thereon which, when executed by a processing device, cause the processing device to:

iteratively:

receive from a user, a response to a prompt issued by a state machine that facilitates interaction by the user with an interactive conversation application, wherein the prompt corresponds to a current state that is one of a plurality of states that the state machine may operate in, and each of the plurality of states corresponds to a conversational objective to be achieved when the state is transitioned to and comprises a corresponding prompt;

extract from the response, metadata including an emotional state of the user, wherein the emotional state of the user corresponds to feelings that the user is experiencing as a result of one or more issues that the user is discussing with the interactive conversation application;

enrich the response with the metadata;

determine a subsequent state from the plurality of states that the state machine is to transition to from the current state based at least in part on the enriched response and the metadata; and transition the state machine to the subsequent state by:
modify the prompt corresponding to the subsequent state based on the enriched response, responses by the user to prompts corresponding to previous states of the state machine, and metadata extracted from the responses by the user to prompts corresponding to previous states of the state machine, wherein the modified prompt includes information from the responses by the user to prompts corresponding to previous states of the state machine; and outputting the modified prompt to the user.

22. The non-transitory computer-readable medium of claim 21, wherein the processing device is further to:
add the metadata to a user database comprising metadata extracted from the responses by the user to prompts corresponding to previous states of the state machine.

23. The non-transitory computer-readable medium of claim 22, wherein the metadata further indicates people, dates, events, and issues that are subjects of the response.

24. The non-transitory computer-readable medium of claim 22, wherein to determine the subsequent state that the state machine is to transition to, the processing device is to:
classify the enriched response; and
determine the subsequent state that the state machine is to transition to based on the classification of the enriched response.

25. The non-transitory computer-readable medium of claim 22, wherein the processing device determines the subsequent state that the state machine is to transition to based further on a previous state of the state machine.

26. The non-transitory computer-readable medium of claim 22, wherein the processing device determines the subsequent state that the state machine is to transition to based further on the responses by the user to prompts corresponding to previous states of the state machine.

27. The non-transitory computer-readable medium of claim 22, wherein the processing device determines the subsequent state that the state machine is to transition to based further on the metadata extracted from the responses by the user to prompts corresponding to previous states of the state machine.

28. The non-transitory computer-readable medium of claim 21, wherein the response comprises one or more of audio data, text data, and video data.

29. The non-transitory computer-readable medium of claim 28, wherein the processing device is further to:
analyze the audio and video data of the response to extract physical indicators of an emotional state of the user; and
add the physical indicators to the metadata.

30. The non-transitory computer-readable medium of claim 29, wherein the physical indicators comprise one or more of: pitch, tone, words per minute, pauses in speech, and changes in volume.

* * * * *